(12) United States Patent
Pratt et al.

(10) Patent No.: US 11,135,342 B2
(45) Date of Patent: Oct. 5, 2021

(54) NEGATIVE-PRESSURE THERAPY WITH PNEUMATICALLY-ACTUATED INSTILLATION

(71) Applicant: KCI Licensing, Inc., San Antonio, TX (US)

(72) Inventors: Benjamin Andrew Pratt, Poole (GB); Christopher Brian Locke, Bournemouth (GB); James Killingworth Seddon, Ferndown (GB)

(73) Assignee: KCI Licensing, Inc., San Antonio, TX (US)

( * ) Notice: Subject to any disclaimer, the term of this patent is extended or adjusted under 35 U.S.C. 154(b) by 890 days.

(21) Appl. No.: 15/520,360

(22) PCT Filed: Oct. 23, 2015

(86) PCT No.: PCT/US2015/057240
§ 371 (c)(1),
(2) Date: Apr. 19, 2017

(87) PCT Pub. No.: WO2016/065335
PCT Pub. Date: Apr. 28, 2016

(65) Prior Publication Data
US 2017/0333605 A1    Nov. 23, 2017

Related U.S. Application Data

(60) Provisional application No. 62/068,425, filed on Oct. 24, 2014.

(51) Int. Cl.
*A61M 5/00*    (2006.01)
*A61M 1/00*    (2006.01)
(Continued)

(52) U.S. Cl.
CPC ..... *A61M 1/0062* (2013.01); *A61F 13/00068* (2013.01); *A61M 1/85* (2021.05);
(Continued)

(58) Field of Classification Search
CPC ........ A61M 5/00; A61M 37/00; A61M 25/16; A61M 1/00; A61M 127/00; A61M 1/0062;
(Continued)

(56) References Cited

U.S. PATENT DOCUMENTS 1,355,846 A    10/1920    Rannells
2,547,758 A     4/1951    Keeling
(Continued)

FOREIGN PATENT DOCUMENTS

AU    550575 B2    3/1986
AU    745271 B2    3/2002
(Continued)

OTHER PUBLICATIONS

ISR and Written Opinion for corresponding PCT/US2015/057240 dated Feb. 19, 2016.
(Continued)

*Primary Examiner* — Michele M Kidwell
*Assistant Examiner* — Ilya Y Treyger

(57) ABSTRACT

New and useful systems, apparatuses, and methods for providing negative-pressure therapy with instillation of topical treatment solutions are described. An apparatus may comprise an exudate container, a solution source, and a pneumatically-actuated instillation regulator. The instillation regulator may be coupled to the exudate container and to the solution source, and negative pressure from a negative-pressure source can actuate the instillation regulator. In some embodiments, a negative-pressure source may be configured for a negative-pressure interval and a venting
(Continued)

interval, and the instillation regulator can be configured to draw instillation solution from the solution source during a negative-pressure interval and to instill the solution to a dressing during a venting interval.

18 Claims, 25 Drawing Sheets

(51) Int. Cl.
*A61F 13/00* (2006.01)
*A61M 37/00* (2006.01)
*A61M 25/16* (2006.01)
*A61F 2/00* (2006.01)
*A61F 2/02* (2006.01)

(52) U.S. Cl.
CPC .............. *A61M 1/90* (2021.05); *A61M 1/964* (2021.05); *A61M 2205/0216* (2013.01); *A61M 2205/3337* (2013.01)

(58) Field of Classification Search
CPC .......... A61M 1/964; A61M 2205/0216; A61M 2205/3337
See application file for complete search history.

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,642 | A | 1/1993 | Clement |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0068913 | A1 | 6/2002 | Fleischmann |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2008/0140029 | A1 | 6/2008 | Smith et al. |
| 2013/0211318 | A1 | 8/2013 | Croizat et al. |

(56) References Cited

U.S. PATENT DOCUMENTS

| | | | |
|---|---|---|---|
| 2014/0163491 A1 | 6/2014 | Schuessler et al. | |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 01/37922 A2 | 5/2001 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its

(56) References Cited

OTHER PUBLICATIONS

Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

NEGATIVE-PRESSURE THERAPY WITH PNEUMATICALLY-ACTUATED INSTILLATION

This present invention is the National Stage of International Application No. PCT/US2015/057240, "NEGATIVE-PRESSURE THERAPY WITH PNEUMATICALLY-ACTUATED INSTILLATION," filed Oct. 23, 2015 and claims the benefit of U.S. Provisional Patent Application Ser. No. 62/068,425, entitled "NEGATIVE-PRESSURE THERAPY WITH PNEUMATICALLY-ACTUATED INSTILLATION," filed Oct. 24, 2014, all of which are incorporated herein by reference for all purposes.

TECHNICAL FIELD

The invention set forth in the appended claims relates generally to tissue treatment systems and more particularly, but without limitation, to apparatuses and methods for providing negative-pressure therapy with instillation of topical treatment solutions.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of a wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and instillation are widely known, the cost and complexity of negative-pressure therapy can be a limiting factor in its application, and the development and operation of negative-pressure systems, components, and processes continues to present significant challenges to manufacturers, healthcare providers, and patients.

BRIEF SUMMARY

New and useful systems, apparatuses, and methods for providing negative-pressure therapy with instillation of topical treatment solutions are set forth in the appended claims. Illustrative embodiments are also provided to enable a person skilled in the art to make and use the claimed subject matter.

For example, an apparatus is described herein that may comprise an exudate container, a solution source, and an instillation regulator that can be pneumatically-actuated. The instillation regulator may be coupled to the exudate container and to the solution source, and negative pressure from a negative-pressure source can actuate the instillation regulator. In some embodiments, for example, a negative-pressure source may be configured for a negative-pressure interval and a venting interval, and the instillation regulator can be configured to draw instillation solution from the solution source during a negative-pressure interval and to instill the solution to a dressing during a venting interval.

In more particular example embodiments, the instillation regulator may have a solution inlet port, a solution outlet port, and a negative-pressure port. The solution inlet port may be fluidly coupled to a solution source, and the solution outlet port may be fluidly coupled to a dressing. The negative-pressure port may be fluidly coupled to a negative-pressure source, which can provide negative pressure through the negative-pressure port to actuate the instillation regulator.

In some example embodiments, the instillation regulator may include a piston disposed within a housing. The piston may partition the housing into a first chamber and a second chamber. The solution inlet port may be fluidly coupled to the solution source and to the first chamber. The solution outlet port may be fluidly coupled to a dressing and to the first chamber. The negative-pressure port may fluidly couple a negative-pressure source to the second chamber, so that negative pressure applied to the second chamber through the negative-pressure port during a negative-pressure interval can actuate the piston. For example, if negative pressure is applied to the second chamber, the pressure differential across the piston can move the piston within the housing, increasing the volume of the first chamber and decreasing the volume of the second chamber. An increase in the volume of the first chamber can decrease the pressure in the first chamber, drawing instillation solution from the solution source through the solution inlet port and into the first chamber. If the pressure in the second chamber is increased, such as during a venting interval, the pressure differential across the piston can reverse the movement of the piston to decrease the volume of the first chamber and increase the volume of the second chamber. Decreasing the volume of the first chamber can increase the pressure in the first chamber, expelling instillation solution from the first chamber through the solution outlet port. Check valves can be coupled to the solution inlet port and the solution outlet port to prevent drawing fluid through the solution outlet port and expelling fluid through the solution inlet port.

In some embodiments, the instillation regulator may be disposed within an exudate container. For example, the instillation regulator may be integrally molded with an exudate container or may be mounted to an interior surface of an exudate container. In yet other example embodiments, the instillation regulator may be configured for coupling between an exudate container and a negative-pressure source.

In some embodiments, instillation solution may be managed as an ancillary to an exudate container, but in other embodiments the instillation solution may be managed integrally to the exudate canister. For example, in some embodiments, a solution source may be externally mounted on an exudate container, but in other example embodiments, a solution source may be disposed within an exudate container.

An apparatus having some or all of these illustrative features may also be used in a system for providing negative-pressure therapy with instillation of topical treatment solutions. For example, a system for treating a tissue site with negative-pressure and instillation therapy may include a dressing, an exudate container, and a negative-pressure source fluidly coupled to the dressing and the exudate container. The system may also include a source of instillation solution. An instillation regulator may be fluidly coupled to the solution source and to the negative-pressure source. Negative pressure from the negative-pressure source can actuate the instillation regulator to draw solution from the solution source. Venting the negative pressure can actuate the instillation regulator to instill the solution to the dressing.

In yet other embodiments, a method for treating a tissue site with negative pressure and topical instillation solution is also describe. For example, a dressing may be applied to the tissue site and coupled to a negative-pressure source. An instillation regulator may also be fluidly coupled to the negative-pressure source and to the dressing. A source of instillation solution may be coupled to the instillation regulator. Solution may be drawn to the instillation regulator from the solution source during a negative-pressure interval, and solution may be instilled from the instillation regulator to the dressing during a venting interval.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
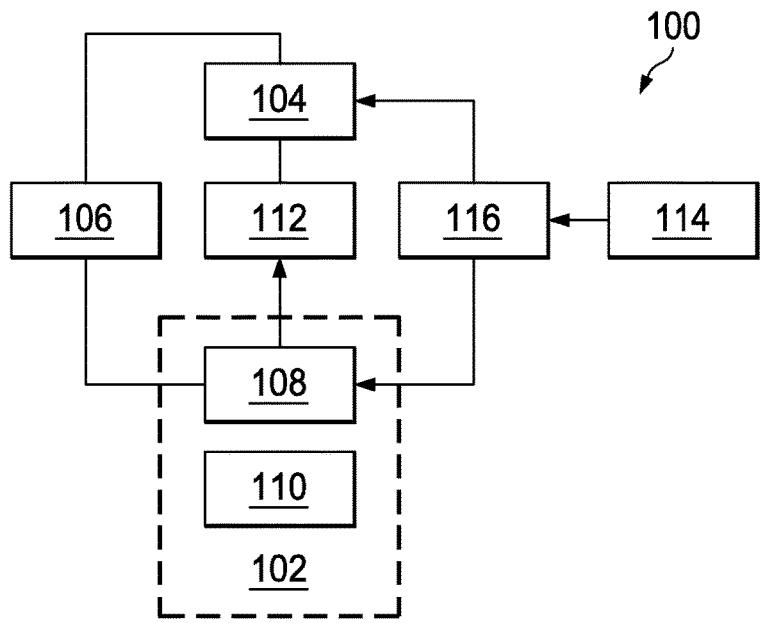
FIG. 1 is a functional block diagram of an example embodiment of a therapy system that can provide negative-pressure therapy and instillation in accordance with this specification.

FIG. 1 is a simplified block diagram of an example embodiment of a therapy system 100 that can provide negative-pressure therapy with instillation of topical treatment solutions in accordance with this specification. The therapy system 100 may include a dressing and a negative-pressure source. For example, a dressing 102 may be fluidly coupled to a negative-pressure source 104, as illustrated in FIG. 1. A regulator, such as a pressure regulator 106, may also be fluidly coupled to the dressing 102 and the negative-pressure source 104. A dressing may include a cover and a tissue interface. The dressing 102, for example, may include a cover 108 and a tissue interface 110. The therapy system 100 may also include an exudate container, such as a container 112, coupled to the dressing 102 and to the negative-pressure source 104.

The therapy system 100 may also include a source of instillation solution. For example, a solution source 114 may be fluidly coupled to the dressing 102, as illustrated in the example embodiment of FIG. 1. A second regulator, such as an instillation regulator 116, may be fluidly coupled to the solution source 114 and the dressing 102. In some embodiments, the instillation regulator 116 may also be pneumatically coupled to the negative-pressure source 104, as illustrated in the example of FIG. 1. The instillation regulator 116 may also be integrated with the container 112 in some embodiments to provide a single, disposable product.

In general, components of the therapy system 100 may be coupled directly or indirectly. For example, the negative-pressure source 104 may be directly coupled to the pressure regulator 106 and indirectly coupled to the dressing 102 through the pressure regulator 106. In some embodiments, components may be coupled by virtue of physical proximity, being integral to a single structure, or being formed from the same piece of material. Coupling may also include mechanical, thermal, electrical, or chemical coupling (such as a chemical bond) in some contexts.

Components may be fluidly coupled to each other to provide a path for transferring fluids (i.e., liquid and/or gas) between the components. In some embodiments, for example, components may be fluidly coupled through a tube. A "tube," as used herein, broadly refers to a tube, pipe, hose, conduit, or other fluid conductor with one or more lumina adapted to convey fluid between two ends. Typically, a tube is an elongated, cylindrical structure with some flexibility, but the geometry and rigidity may vary. A fluid conductor may also be integrally molded into a component in some embodiments.

In operation, the tissue interface 110 may be placed within, over, on, or otherwise proximate to a tissue site. The cover 108 may be placed over the tissue interface 110 and sealed to tissue near the tissue site. For example, the cover 108 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across a tissue site through the tissue interface 110 in the sealed therapeutic environment can induce macro-strain and micro-strain in the tissue site, as well as remove exudate and other fluid from the tissue site, which can be collected in the container 112 and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art.

In general, fluid flows toward lower pressure along a fluid path. Thus, the term "downstream" typically implies something in a fluid path relatively closer to a source of negative pressure or further away from a source of positive pressure; conversely, the term "upstream" implies something relatively further away from a source of negative pressure or closer to a source of positive pressure. Similarly, it may be convenient to describe certain features in terms of fluid "inlet" or "outlet" in such a frame of reference, and the process of reducing pressure may be described illustratively herein as "delivering," "distributing," or "generating" reduced pressure, for example. This orientation is generally presumed for purposes of describing various features and components herein.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, negative pressure may be a pressure less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa). In some embodiments, negative pressure may be applied intermittently or periodically, with intervals of negative-pressure and intervals of venting or positive-pressure.

The tissue interface 110 can be generally adapted to contact a tissue site. The tissue interface 110 may be partially or fully in contact with a tissue site. If a tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites. In some embodiments, the tissue interface may be provided in a spiral cut sheet. Moreover, any or all of the surfaces of the tissue interface 110 may have an uneven, coarse, or jagged profile that can induce micro-strains and stresses at a tissue site.

In some embodiments, the tissue interface 110 may be a manifold. A "manifold" in this context generally includes any substance or structure providing a plurality of pathways adapted to collect or distribute fluid across a tissue site. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate distributing fluid across a tissue site.

In some illustrative embodiments, the pathways of a manifold may be interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and fluid pathways. In some illustrative embodiments, a manifold may be a porous foam material having interconnected cells or pores adapted to distribute negative pressure across a tissue site. The foam material may be either hydrophobic or hydrophilic. The pore size of a foam material may vary according to needs of a prescribed therapy. For example, in some embodiments, the tissue interface 110 may be a foam having pore sizes in a range of 400-600 microns. The tensile strength of the tissue interface 110 may also vary according to needs of a prescribed therapy. For example, the tensile strength of a foam may be increased for instillation of topical treatment solutions. In one non-limiting example, the tissue interface 110 may be an open-cell, reticulated polyurethane foam such as GranuFoam® dressing available from Kinetic Concepts, Inc. of San Antonio, Tex.; in other embodiments the tissue interface 110 may be an open-cell, reticulated polyurethane foam such as a VeraFlo® foam, also available from Kinetic Concepts, Inc., of San Antonio, Tex.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 108 may provide a bacterial barrier and protection from physical trauma. The cover 108 may also be constructed from a material that can reduce evaporative losses and provide a fluid seal between two components or two environments, such as between a therapeutic environment and a local external environment. The cover 108 may be, for example, an elastomeric film or membrane that can provide a seal adequate to maintain a negative pressure at a tissue site for a given negative-pressure source. In some example embodiments, the cover 108 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or an entirety of the cover 108. In some embodiments, for example, some or all of the cover 108 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In some embodiments, the dressing 102 may also include a fluid interface configured to fluidly couple the negative-pressure source 104 to the sealed therapeutic environment formed by the cover 108. In some embodiments, the fluid interface may include a flange portion that couples to the cover 108 and a portion that fluidly couples to a tube 120. In one exemplary embodiment, the fluid interface may be a T.R.A.C.® Pad or Sensa T.R.A.C.® Pad available from Kinetic Concepts, Inc. of San Antonio, Tex. In other exemplary embodiments, a tube may be inserted through the cover 108. Such a fluid interface can allow negative pressure to be delivered to the sealed therapeutic environment. For example, a fluid interface can provide a fluid conductor through the cover 108 to the tissue interface 110. In some embodiments, a fluid interface can also provide more than one fluid path through the cover 108 or merge more than fluid conductor into a single fluid path. For example, in some embodiments, a fluid interface can be fluidly coupled to both the negative-pressure source 104 and to the instillation regulator 116. In one embodiment, such a fluid interface may provide a separate fluid path through the cover 108 for each of the negative-pressure source 104 and the instillation regulator 116. In other embodiments, the fluid interface may merge separate fluid paths from the negative-pressure source 104 and the instillation regulator 116 into a single fluid path through the cover 108.

The container 112 is representative of a container, canister, pouch, or other storage component, which can be used to manage exudate and other fluid withdrawn from a tissue site. In many environments, a rigid container may be preferred or required for collecting, storing, and disposing of fluid. In other environments, fluid may be properly disposed of without rigid container storage, and a re-usable container could reduce waste and costs associated with negative-pressure therapy.

The solution source 114 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

Figure 2:
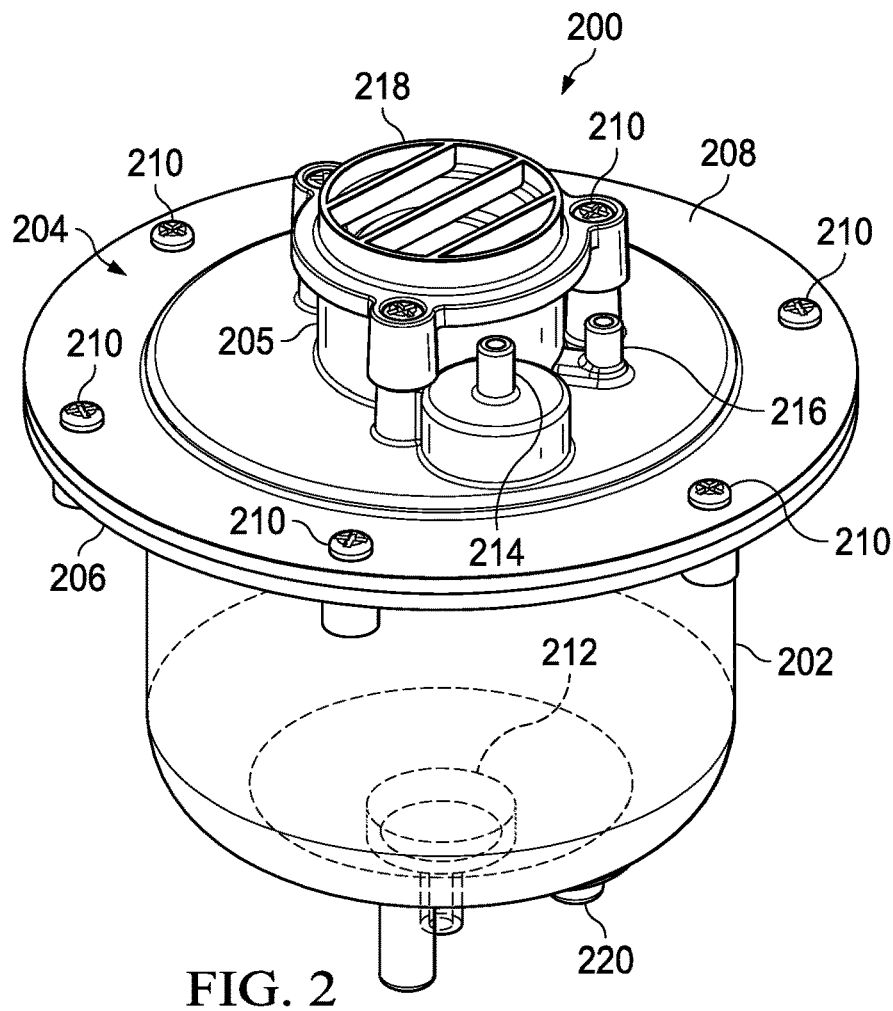
FIG. 2 is a perspective view illustrating additional details that may be associated with some example embodiments of an instillation regulator in the therapy system of FIG. 1.

FIG. 2 is a perspective view of an instillation regulator 200 illustrating additional details that may be associated with some embodiments of the therapy system 100. The instillation regulator 200 may be an example embodiment of the instillation regulator 116 of FIG. 1. The instillation regulator 200 generally includes a housing, which may be formed by a body 202 and a head 204 coupled to the body 202, as shown in the example embodiment of FIG. 2. Some embodiments of the head 204 may include an extension 205. In some embodiments, the body 202 may include a flange 206, and the head 204 may include a flange 208. The body 202 may be cylindrical in some embodiments, as illustrated in the example of FIG. 2, and the head 204 may be circular with a cylindrical extension 205, also as illustrated in the example of FIG. 2. The flange 206 and the flange 208 may be coupled with fasteners 210, or may be coupled with other mechanical, thermal, electrical, or chemical couplings. The dimensions of the flange 208 may be similar to the dimensions of the flange 206 to facilitate a secure coupling.

Some embodiments of the instillation regulator 200 may have fluid ports adapted for coupling to fluid conductor, such as a tube. For example, as shown in FIG. 2, the body 202 may have a negative-pressure port 212, and the head 204 may have a solution inlet port 214 and a solution outlet port 216. A retention cap 218 may also be coupled to the head 204 in some embodiments of the instillation regulator 200, and the body 202 may additionally comprise a vent 220, as shown in the example embodiment of FIG. 2.

Figure 3A:
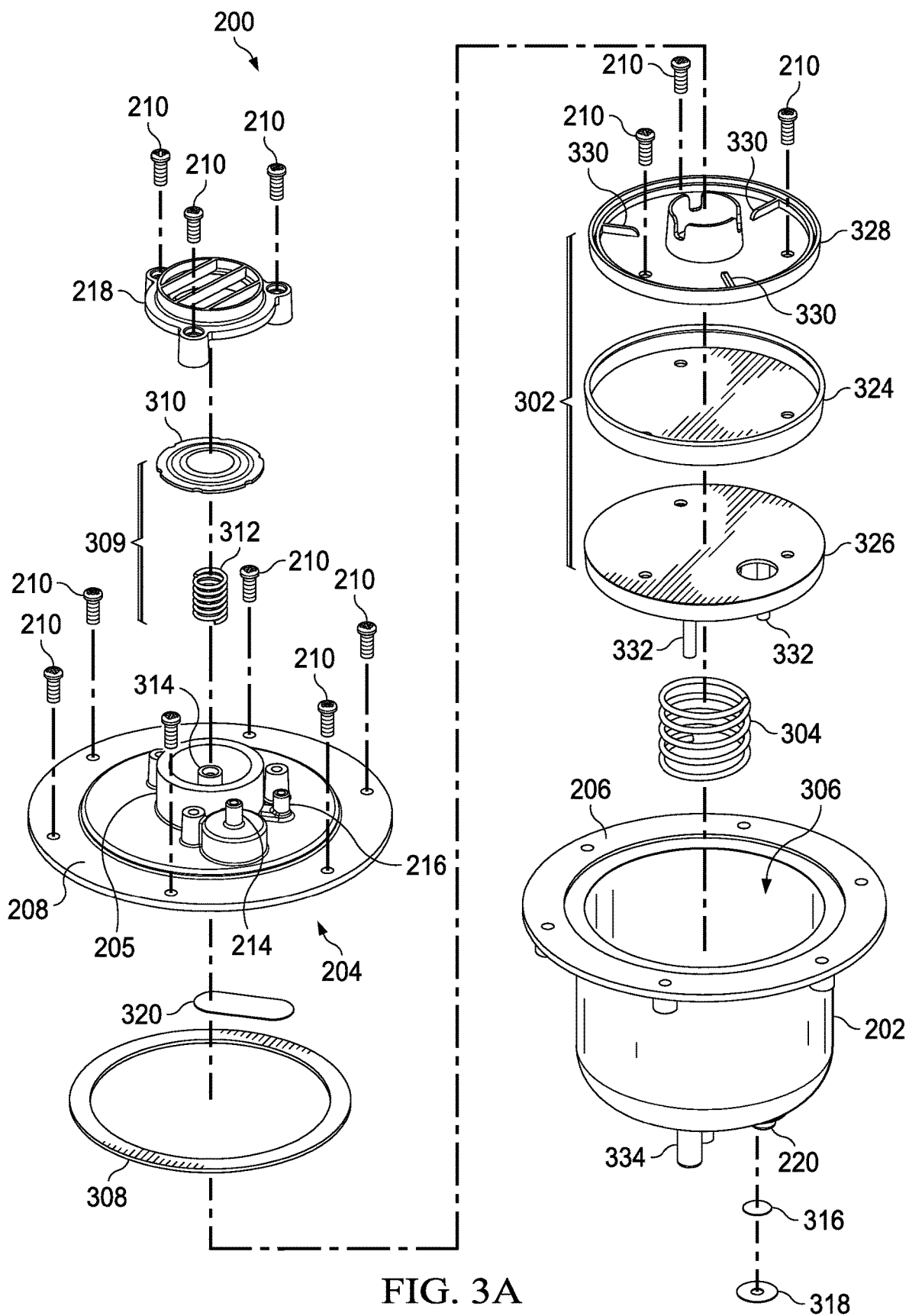
FIGS. 3A-3B are assembly views illustrating additional details that may be associated with some embodiments of the instillation regulator of FIG. 2.
Figure 3B:
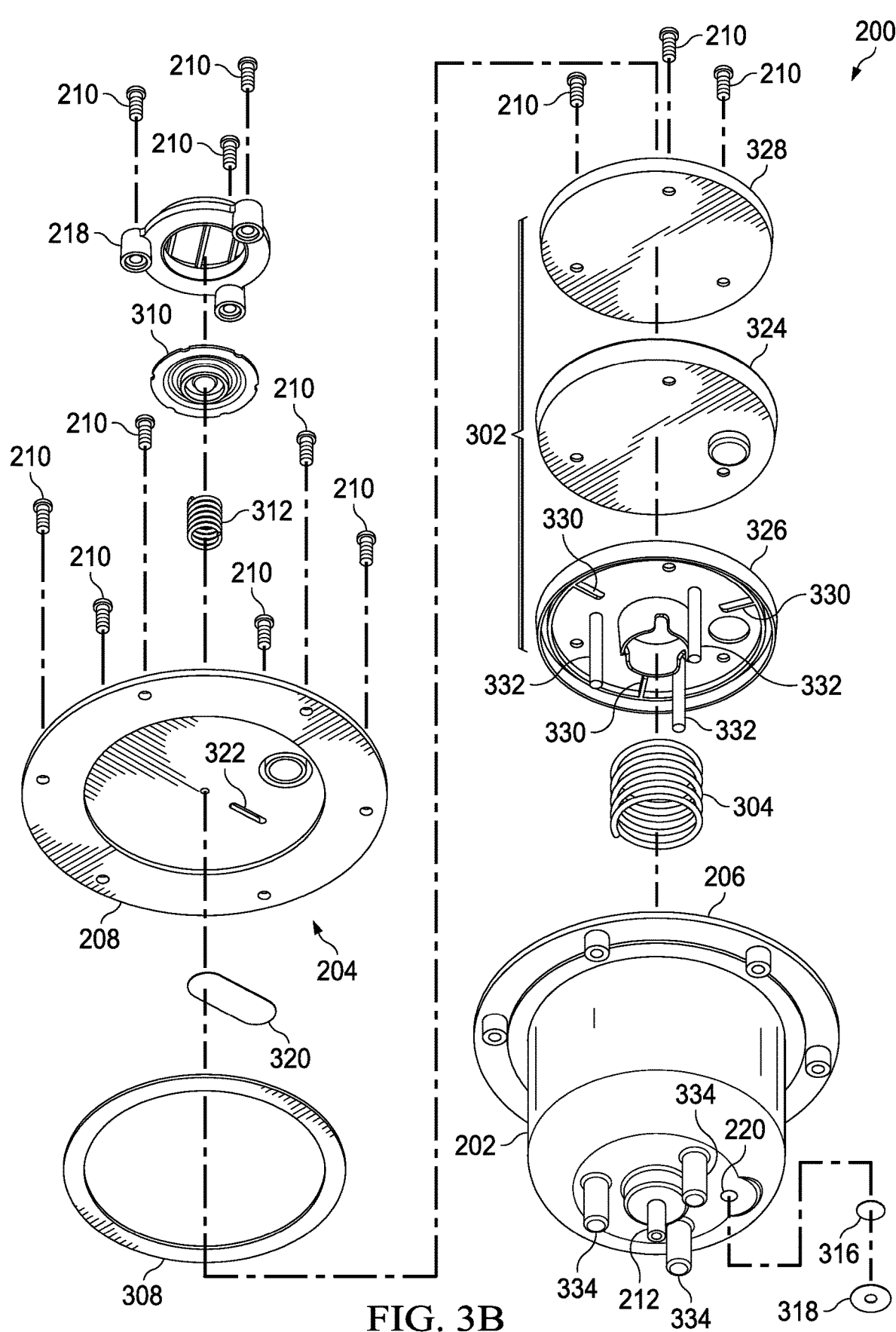

FIG. 3A and FIG. 3B are assembly views illustrating additional details that may be associated with some embodiments of an instillation regulator, such as the instillation regulator 200 of FIG. 2. For example, some embodiments of the instillation regulator 200 may include a piston, an elastic device, and a gasket. A piston can be a flexible or movable barrier, for example, illustrated in FIG. 3A as a piston 302. An elastic device may be a spring or rubber, for example, illustrated in FIG. 3A as a spring 304. The spring 304 may be disposed within a cavity 306 of the body 202, generally between the piston 302 and the body 202, as illustrated in the example embodiment of FIG. 3A. In some embodiments, the spring 304 may be a coil spring coaxial with the piston 302, as shown in the example of FIG. 3A. Also as shown in the example embodiment of FIG. 3A and FIG. 3B, the cavity 306 may be cylindrical, and the piston 302 may be rounded to fit within the cavity 306 of the body 202. The piston 302 may also reciprocate within the cavity 306. A gasket 308 may be disposed between the flange 206 and the flange 208.

The instillation regulator 200 may also include an outlet check valve 309 disposed between the head 204 and the retention cap 218. For example, as shown in the illustrative embodiment of FIG. 3A, some embodiments of the outlet check valve 309 may be a diaphragm valve having a diaphragm 310 and an elastic device such as a spring 312. The diaphragm 310 may be a flexible membrane or partition, such as a thin flexible disk. The spring 312 may be disposed within the extension 205 over a retention boss 314, which can restrict lateral movement of the spring 312.

Some embodiments of the instillation regulator 200 may further include a flow limiter. For example, a flow limiter may comprise a hydrophobic filter 316 and a retaining ring 318, as illustrated in FIG. 3A and FIG. 3B. The hydrophobic filter 316 is generally configured to be disposed in or otherwise engage the vent 220, and the retaining ring 318 may be disposed around or otherwise coupled to the hydrophobic filter and the vent 220 to secure the hydrophobic filter 316 to the vent 220. In some embodiments, a flow limiter may comprise an adjustable valve, such as a needle valve.

The head 204 may include a passage configured to fluidly couple the extension 205 and the solution outlet port 216. For example, the passage may be formed by a membrane 320 coupled to the head 204 to enclose a channel 322 formed in the head 204.

In some embodiments, the piston 302 may comprise a flexible seal disposed between a base and a retainer. For example, the piston 302 of FIG. 3A and FIG. 3B includes a seal 324, a seal base 326, and a seal retainer 328. The seal 324 may be an elastomer or other flexible material, for example, while the seal base 326 and the seal retainer 328 preferably provide strength and rigidity to support the seal 324. In some embodiments, the seal base 326 and the seal retainer 328 may include ribs 330 to provide further structural support. The seal base 326 may include one or more alignment pins 332, which can be configured to engage one or more alignment guides 334.

Figure 4:
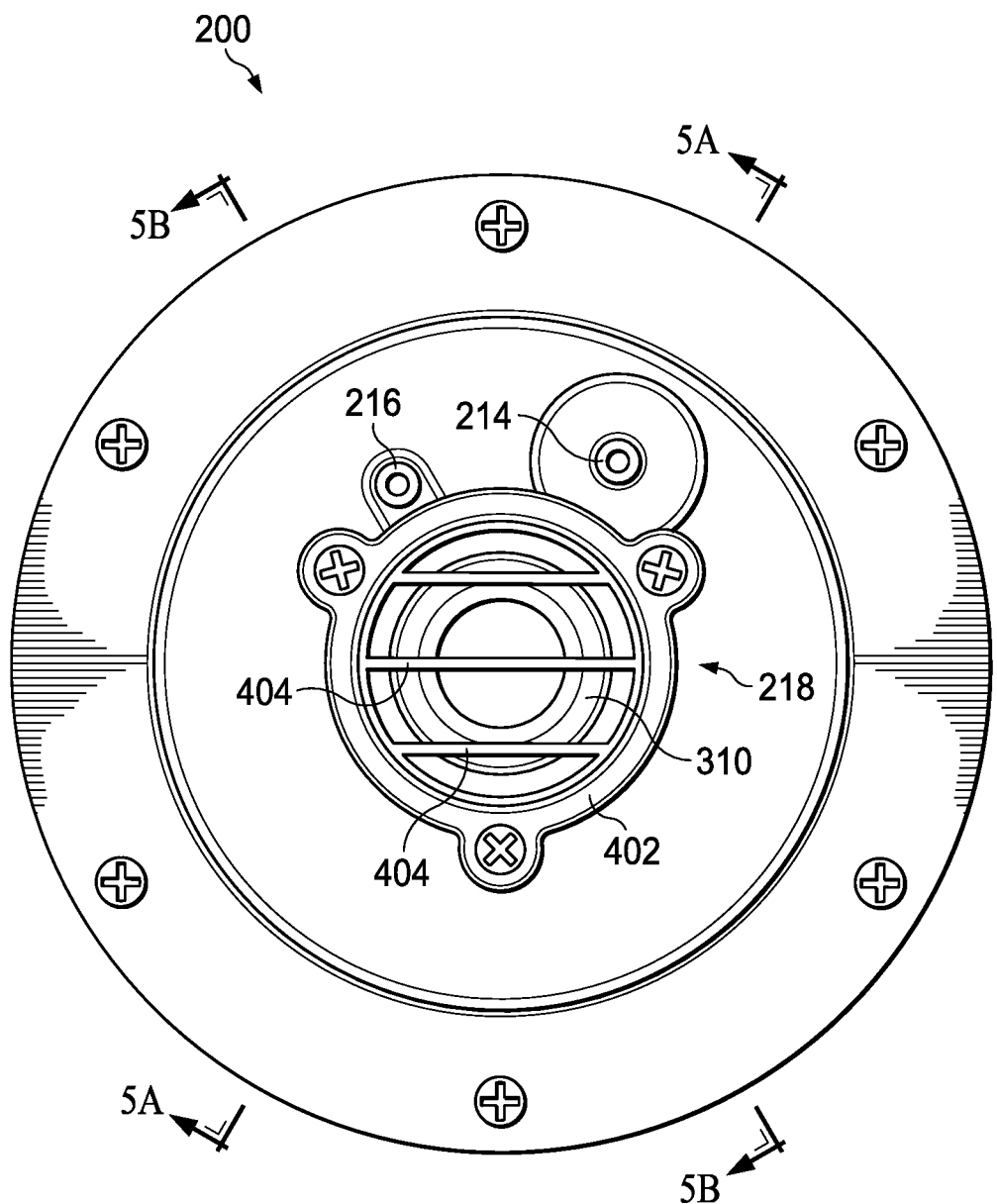
FIG. 4 is a top view illustrating additional details that may be associated with some embodiments of the instillation regulator of FIG. 2.

FIG. 4 is a top view illustrating additional details that may be associated with some embodiments of an instillation regulator, such as the instillation regulator 200. As shown in the example embodiment of FIG. 4, the retention cap 218 may be vented to expose the diaphragm 310 to the ambient environment. In some embodiments, for example, the retention cap 218 may comprise a support ring 402 and cross-bars 404 coupled to the support ring 402. The cross-bars 404 are generally configured to protect the diaphragm 310 and provide a fluid path between the diaphragm 310 and the ambient environment. Additionally or alternatively, a grid, a mesh, or other suitable porous structure may be coupled to the support ring to provide similar protection and fluid communication. The solution inlet port 214 and the solution outlet port 216 may be disposed on, in, or through the head 204, adjacent to the retention cap 218 and outside the support ring 402.

Figure 5A:
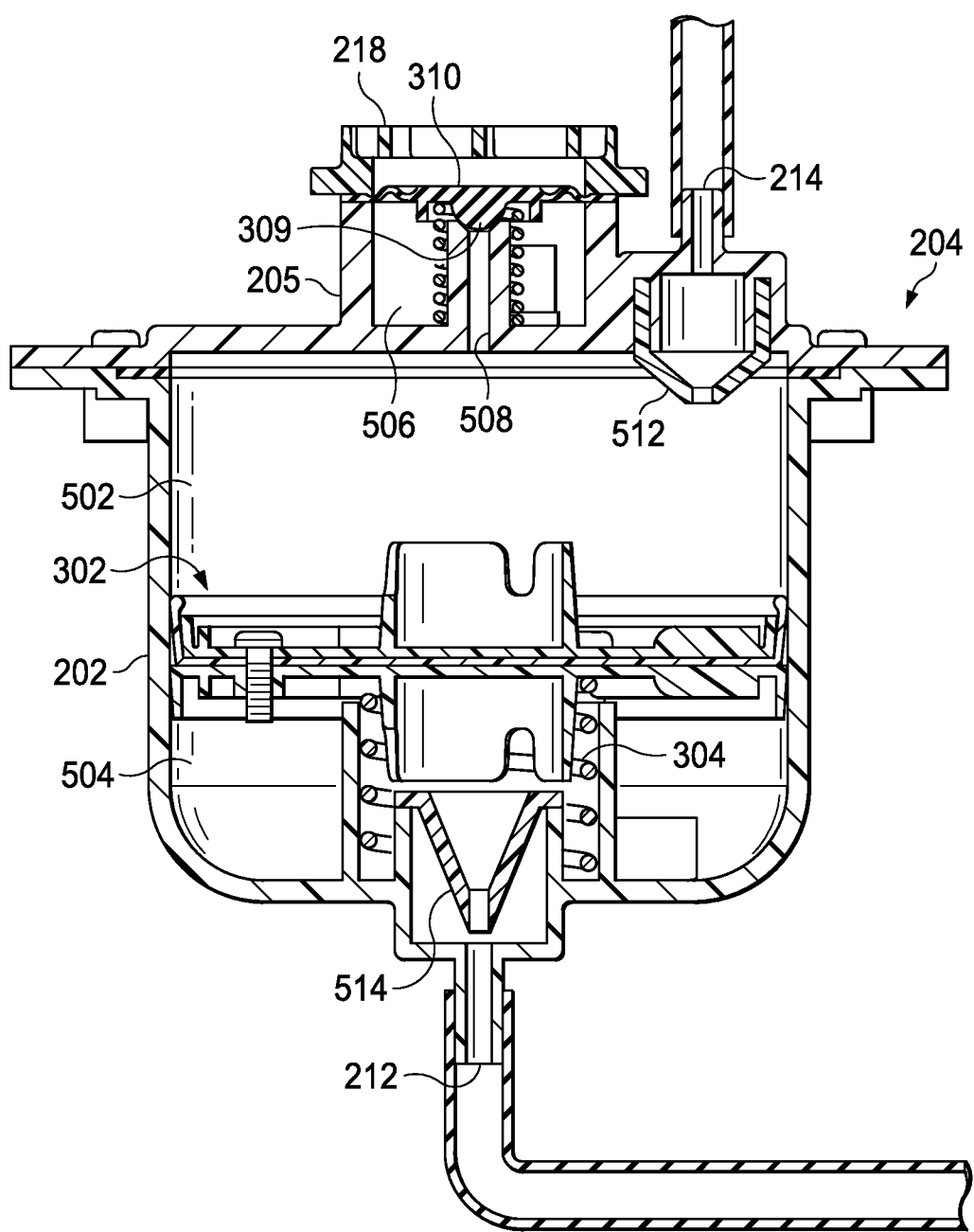
FIG. 5A is a cross-section of the instillation regulator shown in FIG. 4 taken along line 5A-5A.
Figure 5B:
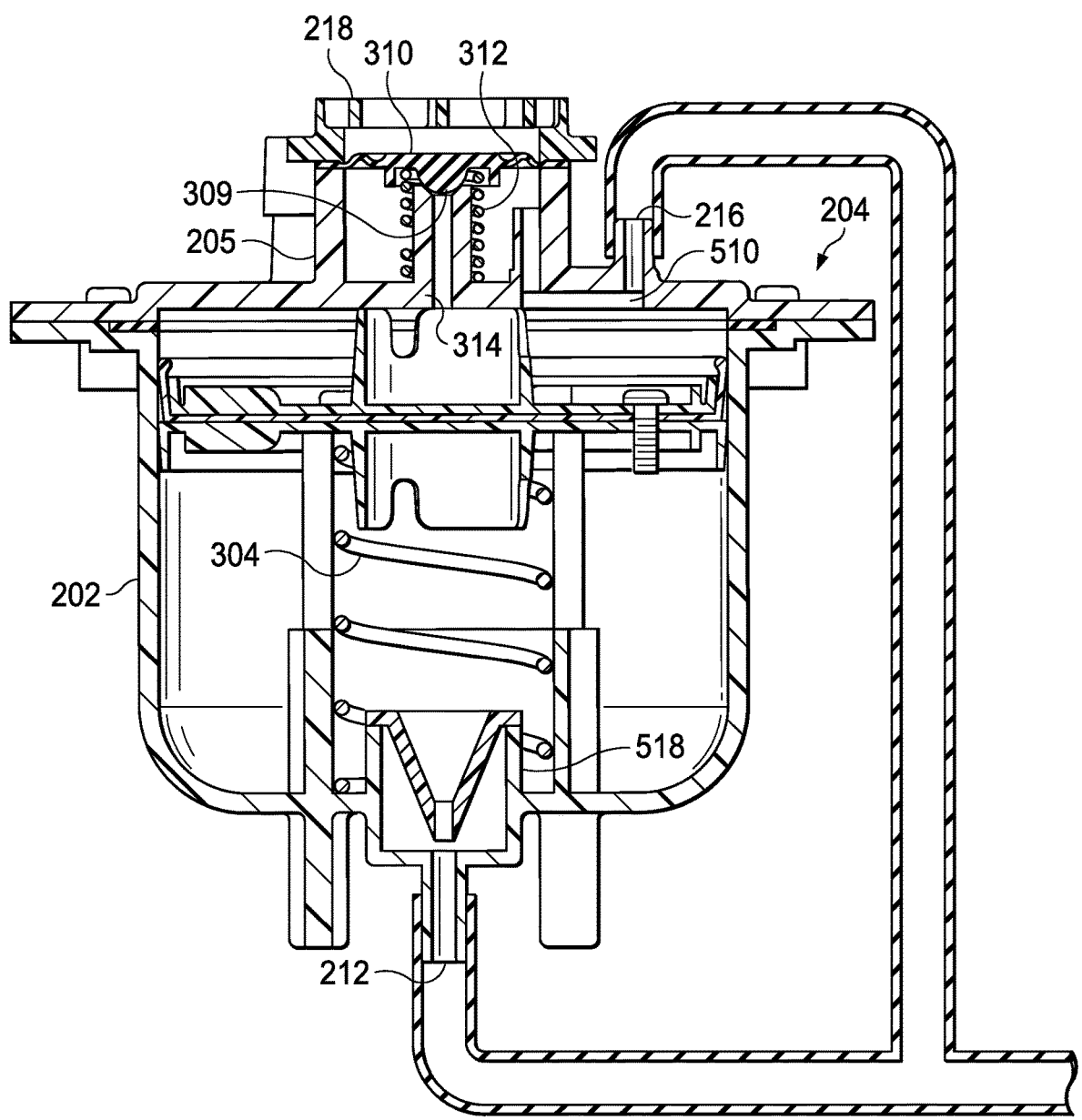
FIG. 5B is a cross-section of the instillation regulator shown in FIG. 4 taken along line 5B-5B.

FIG. 5A is a sectional view of the instillation regulator 200 of FIG. 4 taken on line 5A-5A, illustrating additional details that may be associated with some embodiments of the instillation regulator 200 in a first state. FIG. 5B is a sectional view of the instillation regulator 200 of FIG. 4 taken on line 5B-5B, illustrating additional details that may be associated with some embodiments of the instillation regulator 200 in a second state. Assembled as shown in the example embodiment of FIG. 5A, the head 204 can be coupled to the body 202 to enclose the piston 302 and fluidly isolate the cavity 306 from the ambient environment. The piston 302 may partition or separate the cavity 306 into a first chamber 502 and a second chamber 504. Moreover, the piston 302 may engage the body 202 to provide a seal between the first chamber 502 and the second chamber 504. For example, as shown in the example embodiment of FIG. 5A and FIG. 5B, the seal 324 may press against a side wall of the body 202 to fluidly isolate the first chamber 502 from the second chamber 504.

The diaphragm 310 may be coupled to the extension 205 to form a third chamber 506, generally defined by a portion of the head 204, the extension 205, and the diaphragm 310. The spring 312 may be disposed in the third chamber 506 between the diaphragm 310 and the head 204. For example, the spring 312 may be disposed around the retention boss 314, as shown in the instillation regulator 200 of FIG. 5A and FIG. 5B. In some embodiments, a peripheral edge of the diaphragm 310 may be supported by the extension 205, and an interior portion of the diaphragm 310 may engage the spring 312. The retention cap 218 may be coupled to the head 204 to secure the peripheral edge of the diaphragm 310 between the retention cap 218 and the extension 205. A passage 508 through the retention boss 314 can fluidly couple the first chamber 502 and the third chamber 506 through the outlet check valve 309. A passage 510 in the head 204 may also fluidly couple the third chamber 506 to the solution outlet port 216. The passage 508 and the passage 510 can provide a fluid path between the first chamber 502 and the solution outlet port 216 through the outlet check valve 309, which may be configured to be closed by negative pressure in the first chamber 502.

Some embodiments of the regulator 200 may also include an inlet check valve 512 and an outlet check valve 514. The inlet check valve 512 may be fluidly coupled to the first chamber 502 and configured to be opened by negative pressure in the first chamber 502. The outlet check valve 514 may be fluidly coupled to the second chamber 504 and configured to be opened by negative pressure delivered to the negative-pressure port 212 or by an increase in pressure in the second chamber 504. For example, the inlet check valve 512 may be disposed between the solution inlet port 214 and the first chamber 502, and the outlet check valve 514 may be disposed between the negative-pressure port 212 and the second chamber 504.

The spring 304 may be disposed in the second chamber 504 against the piston 302 and the body 202 to bias the piston. For example, as shown in the illustrative embodiment of FIG. 5A and FIG. 5B, the piston spring 516 may have a first end disposed around a retention boss 518 to restrict lateral movement, and may have a second end engaged to the piston 302. In this example configuration, the spring 304 may bias the piston toward the head 204.

Figure 6:
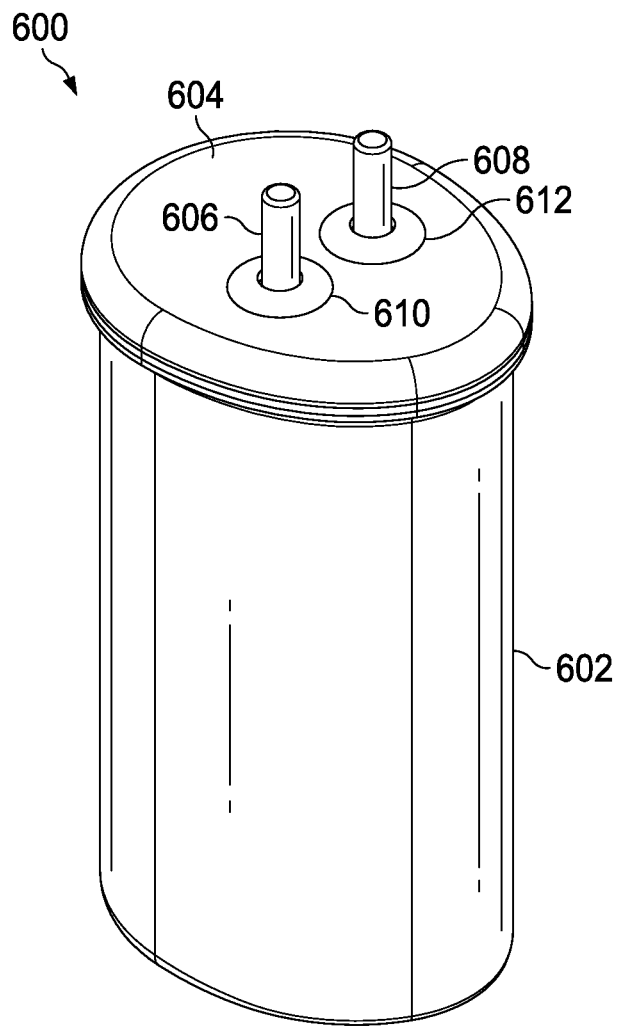
FIG. 6 is a perspective view illustrating additional details of another example embodiment of an instillation regulator that may be associated with the therapy system of FIG. 1.

FIG. 6 is a perspective view of an instillation regulator 600, illustrating details that may be associated with another example embodiment of the instillation regulator 116. The instillation regulator 600 generally includes a housing, which may be formed by a body 602 and a cap 604 coupled to the body 602, as shown in the example embodiment of FIG. 6. Some embodiments of the instillation regulator 600 may have fluid ports adapted for coupling to a tube or other fluid conductor. For example, as shown in FIG. 6, the instillation regulator 600 may have a first fluid port, such as the solution inlet port 606, which may extend through an inlet port opening 610 of the cap 604, and a second fluid port, such as the solution outlet port 608, which may extend through an outlet port opening 612.

Figure 7A:
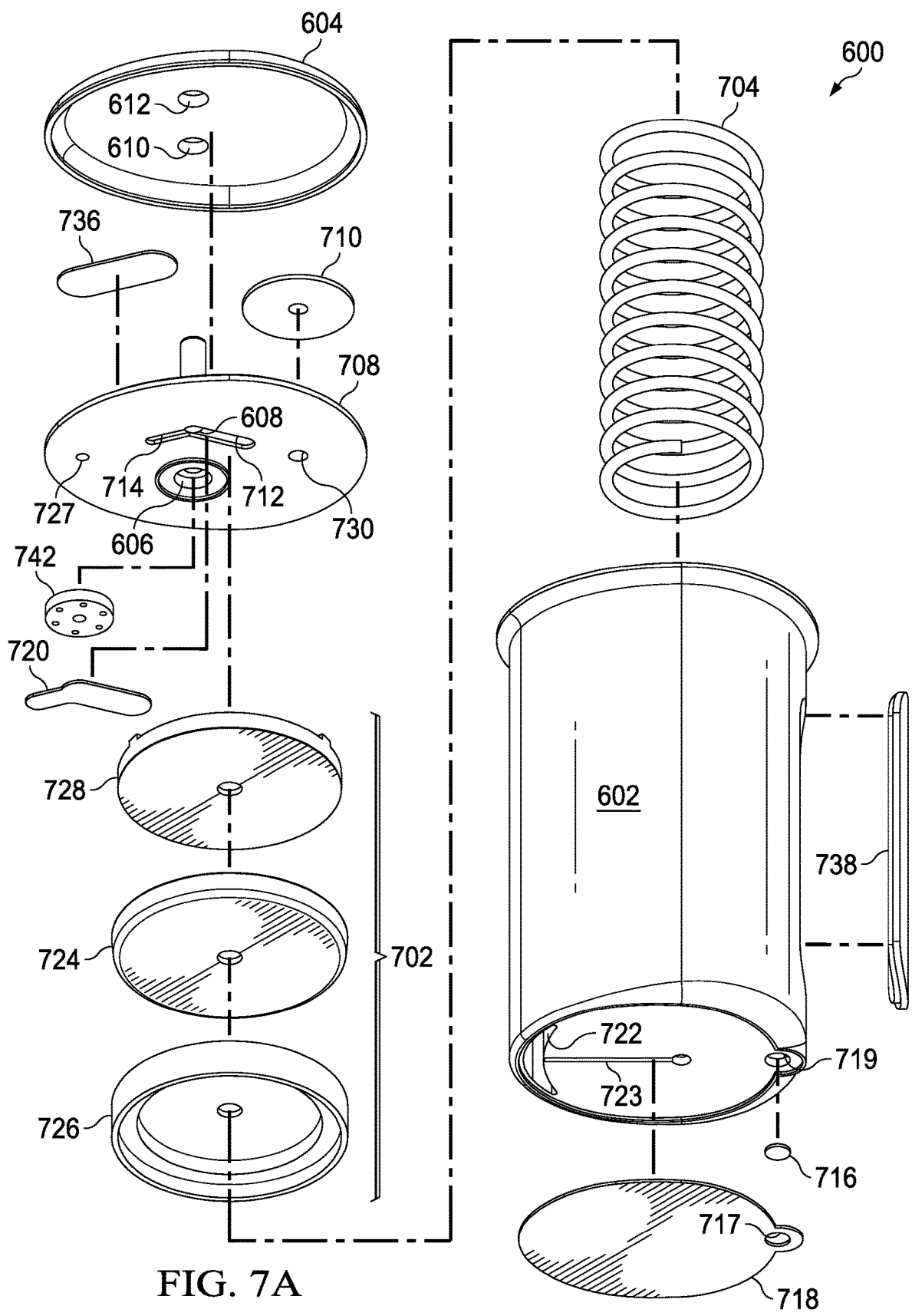
FIGS. 7A-7B are assembly views illustrating additional details that may be associated with some embodiments of the instillation regulator of FIG. 6.
Figure 7B:
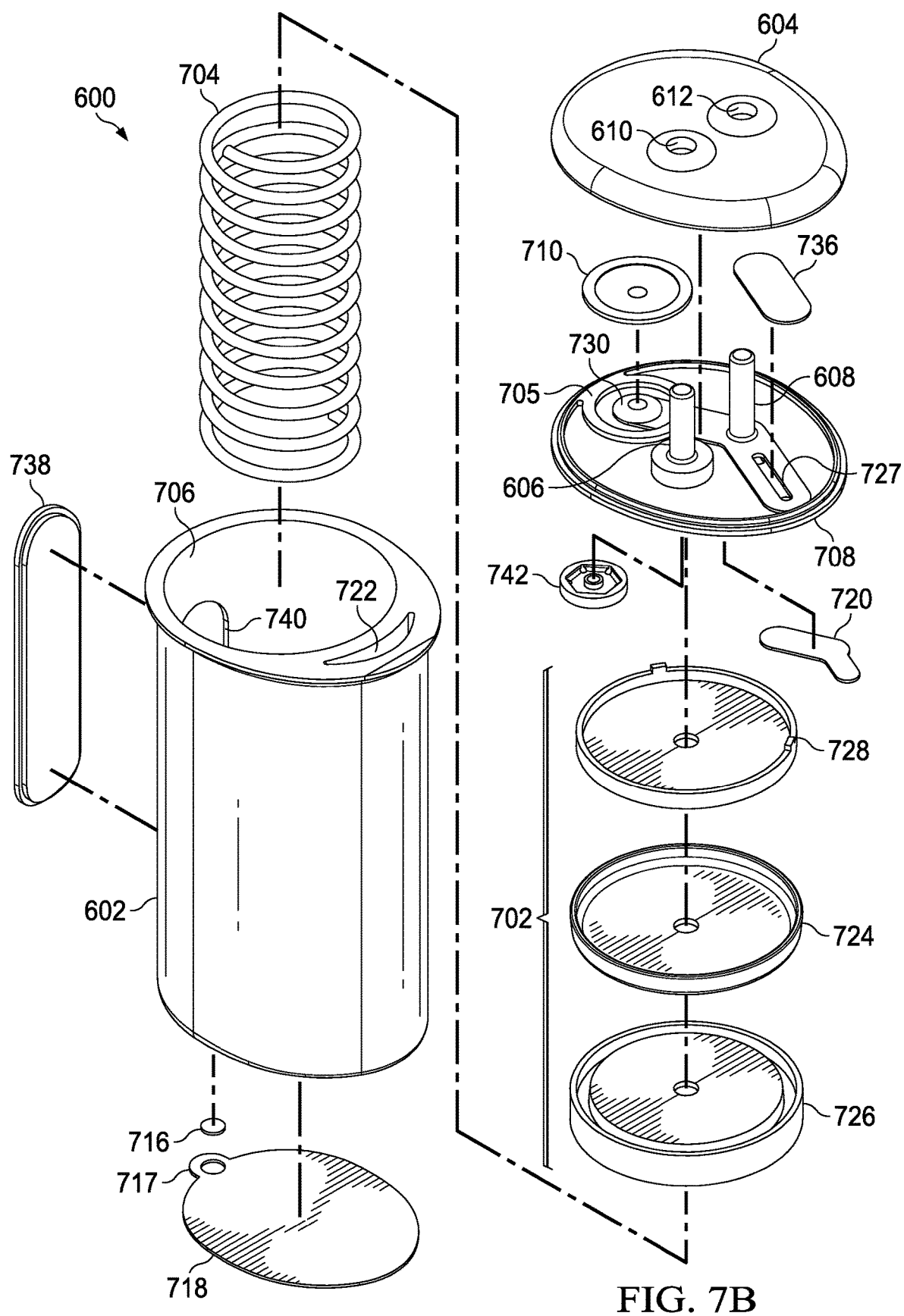

FIG. 7A and FIG. 7B are assembly views illustrating additional details that may be associated with some embodiments of an instillation regulator, such as the instillation regulator 600 of FIG. 6. Some embodiments of the instillation regulator 600 may include a piston, an elastic device, and a gasket. The piston can be a flexible or movable barrier, for example, illustrated in FIG. 7A as a piston 702. An elastic device may be a spring or rubber, for example, illustrated in FIG. 7A as a spring 704. The spring 704 may be disposed within a cavity 706 of the body 602 of the instillation regulator 600, generally between the piston 702 and the body 602, as illustrated in the example embodiment of FIG. 7B. In some embodiments, the spring 704 may be a coil spring coaxial with the piston 702, as shown in the example of FIG. 7A. Also as shown in the example embodiment of FIG. 7A and FIG. 7B, the cavity 706 may be a cylindrical bore, and the piston 702 may be rounded to fit within the cavity 706 of the body 602. The piston 702 may also reciprocate within the cavity 706.

The body 602 of the instillation regulator 600 may also comprise a window 738, which may allow viewing the interior of the instillation regulator 600 through an opening 740. For example, the position of the piston 702 or the fluid in the cavity 706 may be viewed through the window 738 and the opening 740 in some embodiments.

The instillation regulator 600 may also include a head 708, which may be disposed between the body 602 and the cap 604. The instillation regulator 600 may also include an outlet check valve 710 disposed between the head 708 and the cap 604. For example, the outlet check valve 710 may be a diaphragm valve comprising a flexible membrane or partition, such as a thin flexible disk. A membrane 736 may also be disposed between the cap 604 and a channel 727 of the head 708. The head 708 may comprise an extension 705, and a valve seat 730 within the extension 705 configured to engage the outlet check valve 710.

Some embodiments of the instillation regulator 600 may also include a flow limiter. For example, a flow limiter may comprise a hydrophobic filter 716, as illustrated in FIG. 7A and FIG. 7B. The hydrophobic filter 716 is generally configured to be disposed in or otherwise engage a vent 719, and a retaining ring 717 may be disposed around or otherwise coupled to the hydrophobic filter 716 and the vent 719 to couple the hydrophobic filter 716 to the vent 719. The retaining ring 717 may be coupled to or integral with a sealing membrane 718, as illustrated in the example embodiment of FIG. 7A and FIG. 7B.

The head 708 may also include a passage configured to fluidly couple the valve seat 730 to the solution outlet port 608. For example, an integrated fluid conductor may be formed by a membrane 720 coupled to the head 708 to enclose a channel 712 formed in the head 708. Another passage may fluidly couple the solution outlet port 608 to the channel 727. For example, an integrated fluid conductor may be formed by coupling the membrane 720 to the head 708 to enclose a channel 714. The membrane 736 may also be coupled to the head 708 to enclose the channel 727. In some embodiments, any or all of the channel 712, the channel 714 and the channel 727 may be integrally molded into the head 708.

The body 602 may also include one or more passages configured to fluidly couple the channel 727 to the cavity 706. For example, the body 602 may include a fluid conductor formed by the sealing membrane 718 coupled to the body 602 to enclose a channel 723, and a passage 722 in the body 602 may fluidly couple the channel 723 and the channel 727. In some embodiments, either or both of the passage 722 and the channel 723 may be integrally molded in the body 602.

In some embodiments, the piston 702 may comprise a conformable seal disposed between a base and a retainer. For example, the piston 702 of FIG. 7A and FIG. 7B includes a seal 724, a seal base 726, and a seal retainer 728. The seal 724 may be an elastomer or other flexible material, for example, while the seal base 726 and the seal retainer 728 may be a rigid plastic to provide strength and rigidity to support the seal 724. An inlet check valve 742 may also be disposed between the head 708 and the seal retainer 728, fluidly coupled to the solution inlet port 606.

Figure 8:
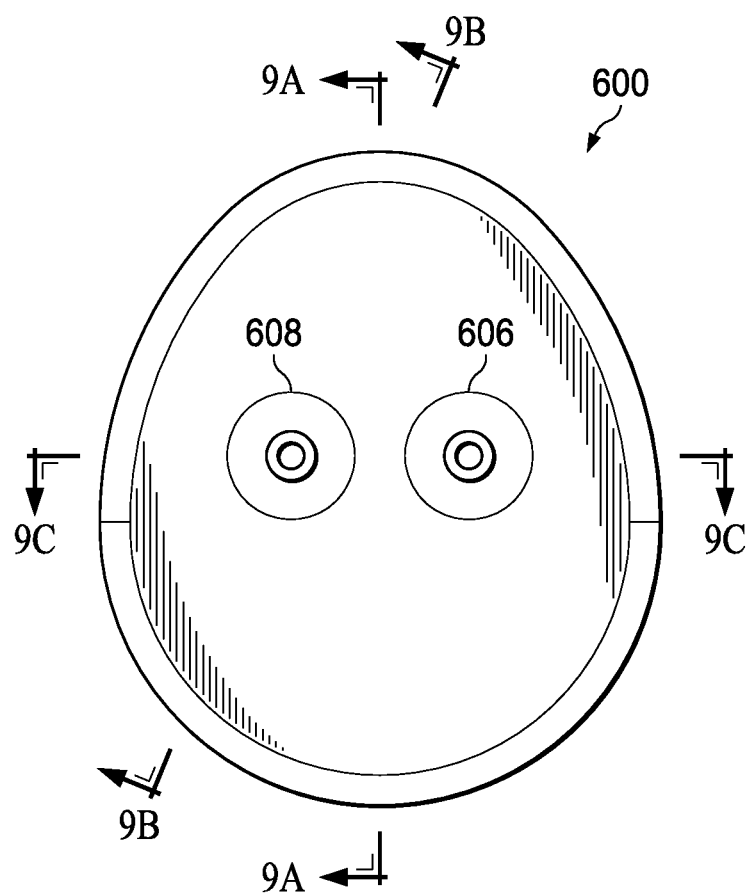
FIG. 8 is a top view illustrating additional details that may be associated with some embodiments of the instillation regulator of FIG. 6.

FIG. 8 is a top view illustrating additional details that may be associated with some embodiments of an instillation regulator, such as the instillation regulator 600. As illustrated in the example embodiment of FIG. 8, the instillation regulator 600 may have an ovate profile to accommodate the cavity 706 and the passage 722.

Figure 9A:
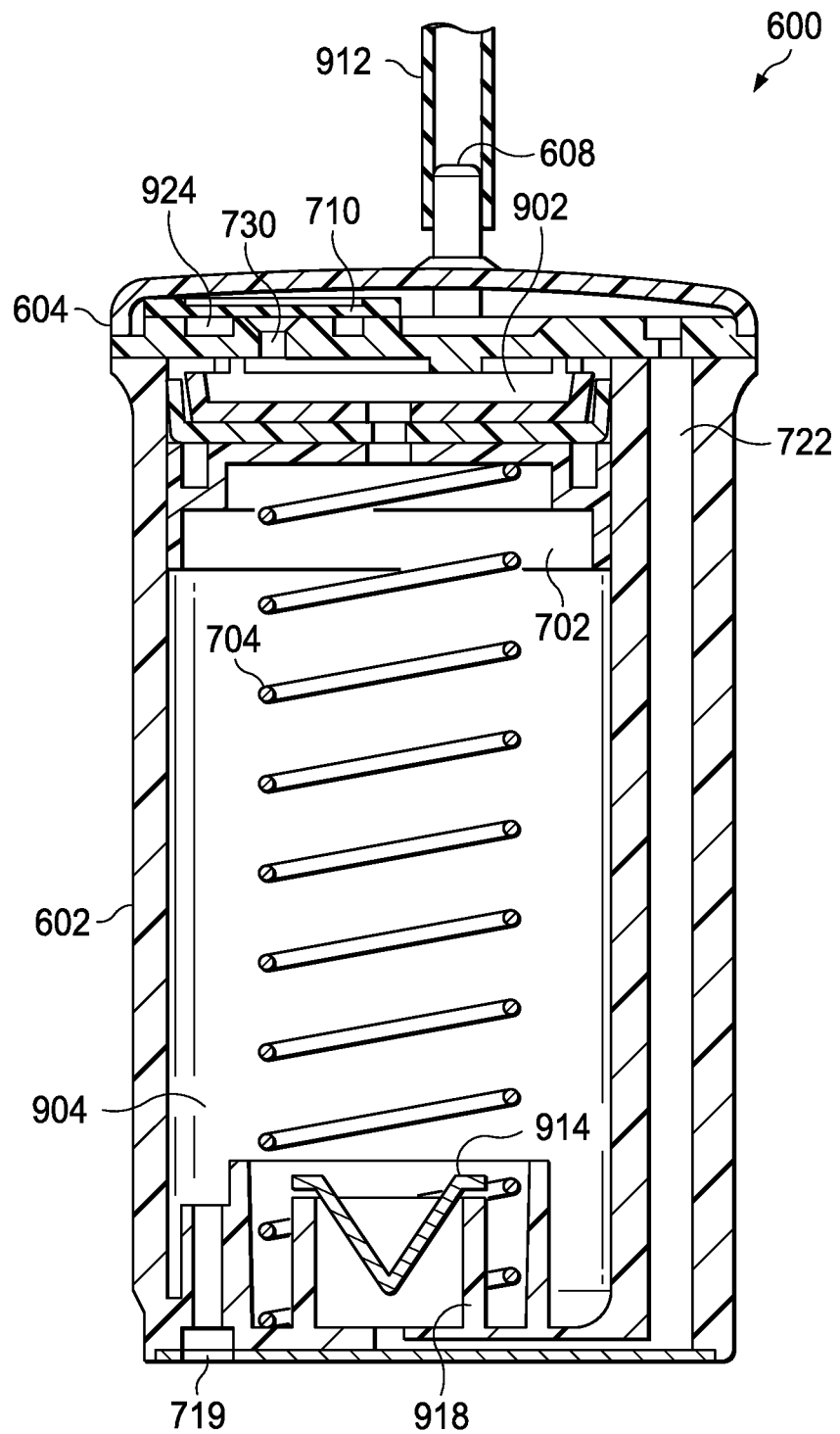
FIG. 9A is a cross-section of the instillation regulator shown in FIG. 8 taken along line 9A-9A.
Figure 9B:
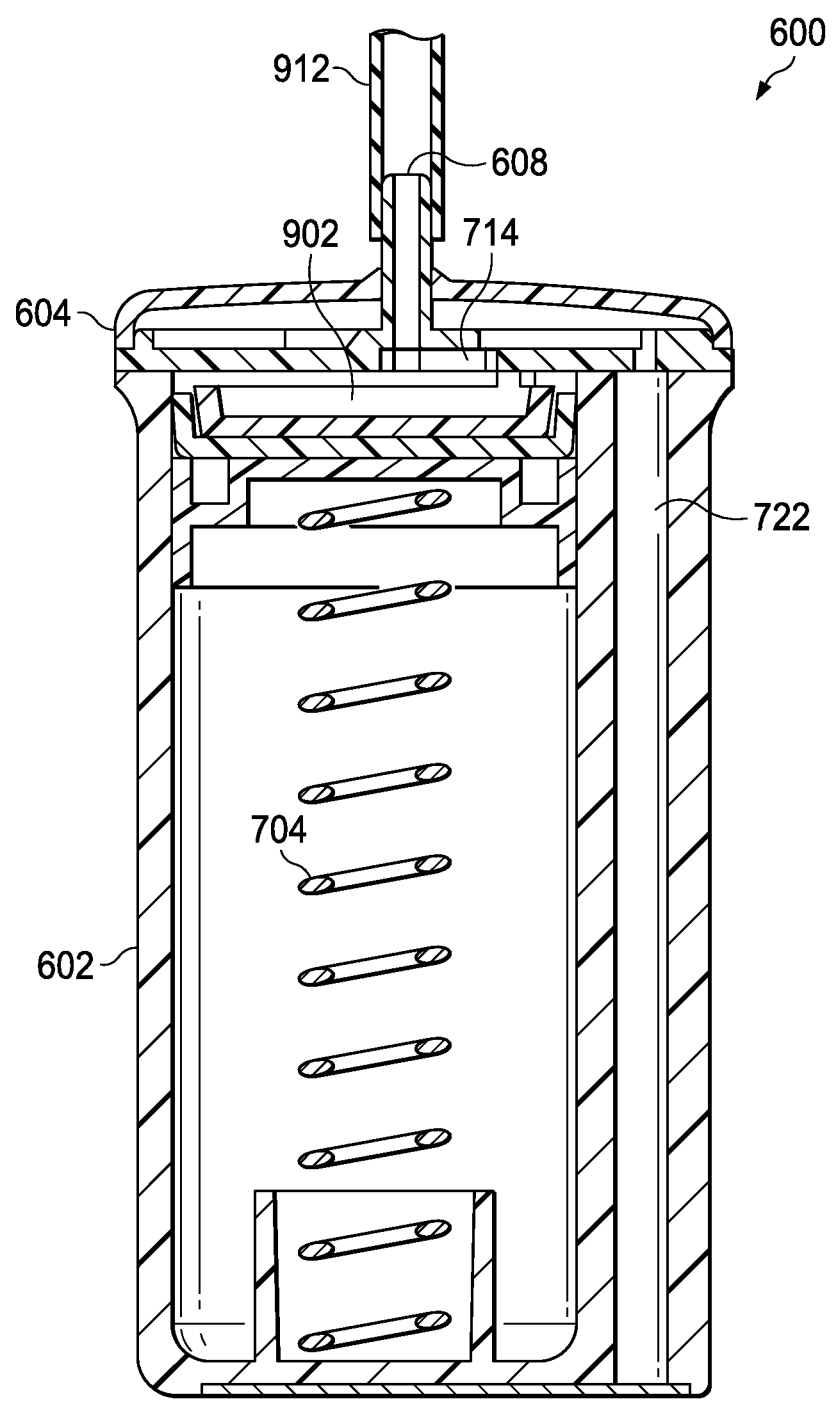
FIG. 9B is a cross-section of the instillation regulator shown in FIG. 8 taken along line 9B-9B.
Figure 9C:
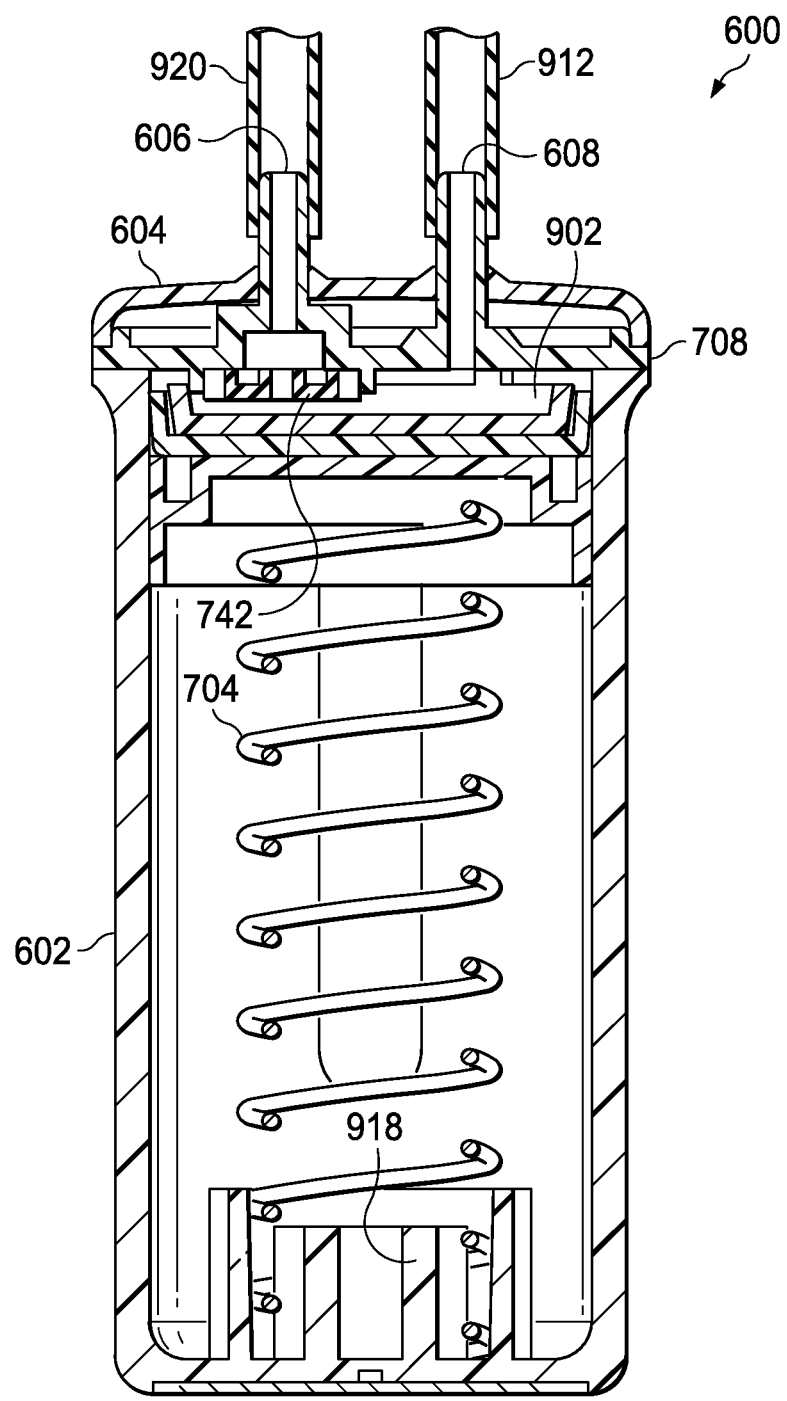
FIG. 9C is a cross-section of the instillation regulator shown in FIG. 8 taken along line 9C-9C.

FIG. 9A is a sectional view of the instillation regulator 600 of FIG. 8 taken on line 9A-9A, illustrating additional details that may be associated with some embodiments of the instillation regulator 600. FIG. 9B is a sectional view of the instillation regulator 600 of FIG. 8 taken on line 9B-9B, illustrating additional details that may be associated with some embodiments of the instillation regulator 600. FIG. 9C is a sectional view of the instillation regulator 600 of FIG. 8 taken on line 9C-9C, illustrating additional details that may be associated with some embodiments of the instillation regulator 600. Assembled as shown in the example embodiment of FIG. 9A, the head 708 can be coupled to the body 602 to fluidly isolate the cavity 706 from the ambient environment, and the piston 702 may partition or separate the cavity 706 into a first chamber 902 and a second chamber 904. Moreover, the piston 702 may engage the body 602 to provide a seal between the first chamber 902 and the second chamber 904. For example, as shown in the example embodiment of FIG. 9A, the seal 724 may press against a side wall of the body 602 to fluidly isolate the first chamber 902 from the second chamber 904.

The outlet check valve 710 may be coupled to the extension 705 to form a third chamber 924, generally defined by a portion of the head 708, the extension 705, and the outlet check valve 710. In some embodiments, a peripheral edge of the outlet check valve 710 may be supported or coupled to the extension 705. Additionally or alternatively, the cap 604 can be disposed on the head 708 to secure the outlet check valve 710 to the extension 705. A passage through the valve seat 730 may fluidly couple the first chamber 902 and the third chamber 924. The channel 712 may also fluidly couple the third chamber 924 to the solution outlet port 608.

The inlet check valve 742 may be fluidly coupled to the first chamber 902 and configured to be opened by negative pressure in the first chamber 902. Some embodiments may also comprise an outlet check valve 710 fluidly coupled to the second chamber 904 and configured to be opened by negative pressure in the channel 723 or by an increased pressure in the second chamber 904. For example, the inlet check valve 742 may be disposed between the solution inlet port 606 and the first chamber 902, and the outlet check valve 914 may be disposed between the solution outlet port 608 and the second chamber 904.

The spring 704 may be disposed between the piston 702 and the body 602 in some embodiments. For example, as shown in the illustrative embodiment of FIGS. 9A-9C, the spring 704 may have a first end disposed around a retention boss 918 to restrict lateral movement, and may have a second end engaged to the piston 702.

In operation, the instillation regulator 600 may be primed during negative-pressure intervals, and may instill a solution during venting intervals. For example, during a negative-pressure interval, negative pressure can be supplied by a negative-pressure therapy unit (not shown) and delivered by a tube 912 to the instillation regulator 600. In the embodiment of FIGS. 9A-9C, negative pressure may be delivered to the second chamber 904 through the solution outlet port 608, the passage 722, and the channel 723. Negative pressure in the second chamber 904 can move the piston 702, expanding the first chamber 902 and compressing the second chamber 904. If the first chamber 902 expands, pressure in the first chamber 902 can decrease proportionately. Negative pressure in the first chamber 902 can have the effect of actively drawing instillation solution into the first chamber 902 through the solution inlet port 606. The distance that the piston 702 travels can determine a dosage volume of instillation solution. The first chamber 902 may be lined with a suitable material to prevent contamination from mechanical components or lubricants. For example, the first chamber 902 may be lined with a film bag, an elastomeric bag, or a compressible bellows.

In some embodiments, the instillation dosage may be adjusted. Such capability may be achieved by adjusting the distance traveled of the movable components during negative-pressure and venting intervals. For example, the spring 704 may be compressed so that the distance traveled by the piston 702 can be limited. This may result from more quickly reaching the point where the negative pressure applied to the second chamber 904 for compressing the spring 704 can no longer overcome the force exerted by the spring 704. Other example embodiments may adjust the instillation dosage by reducing the height of the second chamber 904, for example, by screwing the first chamber 902 further into the second chamber 904 using a threaded mechanism. Yet another example may include controlling the dosage of instillation fluid delivered by limiting the travel of the piston 702 within the second chamber 904 by adjusting the height of a stop block located within the second chamber 904, under the piston 702. Additional examples may include restricting the flow of instillation fluid through either the solution inflow tube 920 or the solution outflow tube 912 using, for example, a valve, or by restricting the rate at which the piston 702 recovers.

Expansion of the first chamber 902 may also have the effect of decreasing pressure in the third chamber 924, as pressure between the first chamber 902 and the third chamber 924 may be equalized through the passage 926. The decreased pressure in the third chamber 924 may have the effect of closing the outlet check valve 710, which can prevent instillation of solution to a dressing during a negative-pressure interval.

During a venting interval, the vent 719 may provide fluid communication between the second chamber 904 and the ambient environment, which can also have the effect of increasing pressure in the second chamber 904. Increased pressure in the second chamber 904 during a venting interval can have the effect of moving the piston 702, compressing the first chamber 902 and expanding the second chamber 904. If the first chamber 902 is compressed, pressure in the first chamber 902 can increase proportionately. The resulting increase in pressure can move solution out of the first chamber 902 through the valve seat 730, the channel 712, and the solution outlet port 608, instilling solution to a tissue site through the solution outflow tube 912. The inlet check valve 742 can prevent back-flow through the solution inlet port 606 during instillation, and the outlet check valve 914 can prevent solution from moving into the second chamber 904 from the channel 723 during instillation. A flow limiter such as the hydrophobic filter 716 can control the rate of venting between the second chamber 904 and the ambient environment through the vent 719, which can also determine the rate at which the piston 702 moves and the rate at which solution can be instilled from the first chamber 902. For example, the surface area of the hydrophobic filter 716 can determine the vent rate and can be calibrated to provide a prescribed instillation rate.

Figure 10:
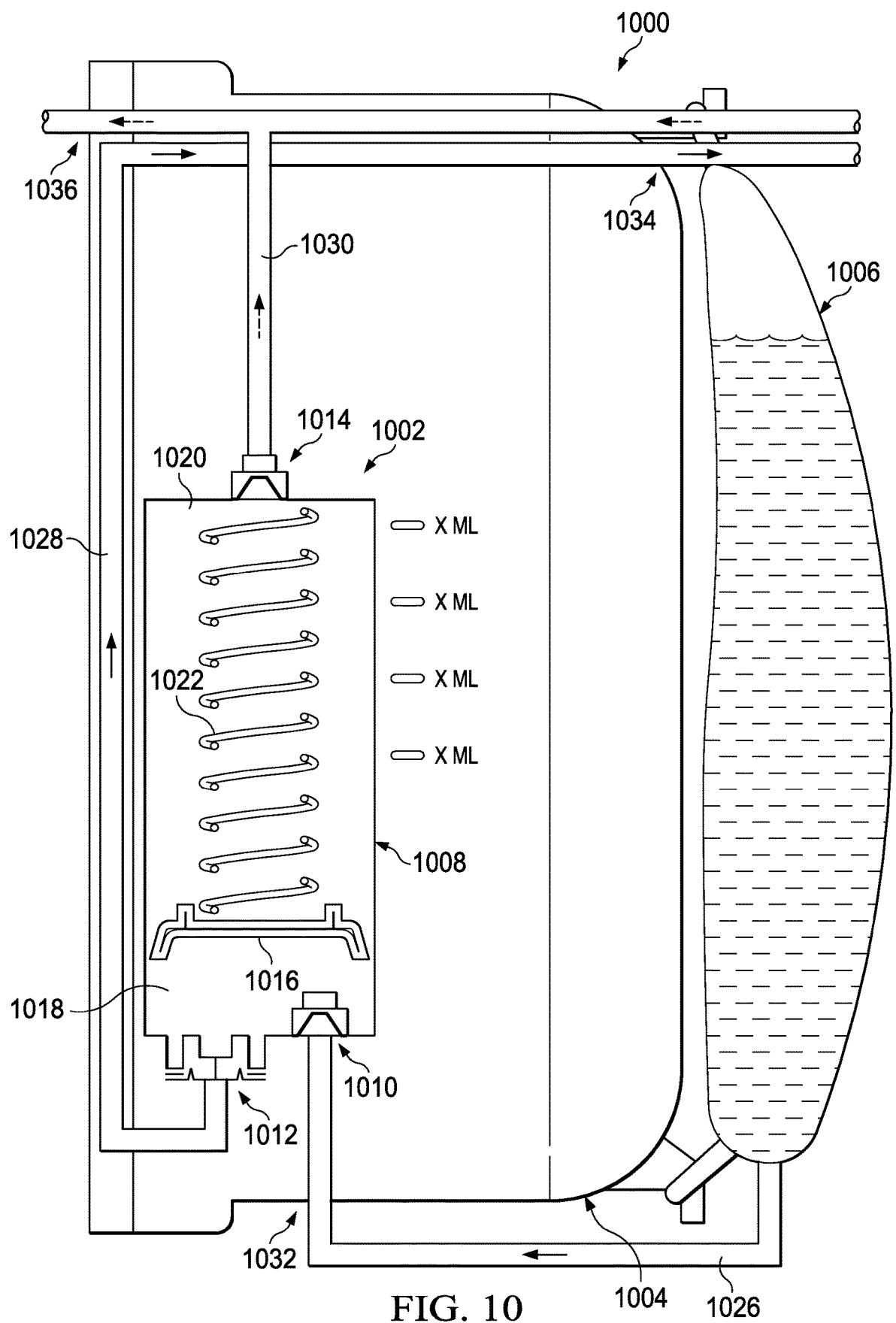
FIG. 10 is a schematic diagram illustrating an example embodiment of a fluid management system comprising an instillation regulator disposed within an exudate container.

FIG. 10 is a schematic diagram illustrating an example embodiment of a fluid management system 1000 comprising an installation regulator 1002 disposed within an exudate container 1004. The installation regulator 1002 is an example embodiment of the installation regulator 116 of FIG. 1, and the exudate container 1004 may be an example embodiment of the container 112 of FIG. 1. The fluid management system 1000 may also include an ancillary installation solution source, such as a solution bag 1006. The solution bag 1006 may be an example embodiment of the solution source 114 of FIG. 1. In some embodiments, the solution bag 1006 may be externally mounted on the exudate container 1004, as illustrated in FIG. 10. In other embodiments, the solution bag 1006 may be secured to a pole or other hanger, preferably in close proximity to the exudate container 1004.

The installation regulator 1002 may be analogous in many respects to the installation regulator 200 or the installation regulator 600. For example, the installation regulator 1002 may include a housing 1008, a solution inlet port 1010, a solution outlet port 1012, and a negative-pressure port 1014. The installation regulator 1002 may also include a piston 1016 disposed in a cavity of the housing 1008. The piston 1016 may partition or separate the cavity into a first chamber 1018 and a second chamber 1020. Moreover, the piston 1016 may engage the housing 1008 to provide a seal between the first chamber 1018 and the second chamber 1020. A spring 1022 may be disposed between the piston 1016 and the housing 1008, as illustrated in the example embodiment of FIG. 10. The piston 1016 may reciprocate within the housing 1008, varying the volume of the first chamber 1018 and the second chamber 1020.

As illustrated in FIG. 10, the installation regulator 1002 may be disposed within an interior space of the exudate container 1004 in some embodiments. For example, the installation regulator 1002 may be fastened to a wall of the exudate container 1004, or may be integrally molded with the exudate container 1004. The installation regulator 1002 may also be fluidly coupled to the solution bag 1006, to a dressing (not shown in FIG. 10), and to a negative-pressure source (not shown in FIG. 10). For example, in some embodiments, the fluid management system 1000 may provide a fluid path 1026 between the solution bag 1006 and the solution inlet port 1010, a fluid path 1028 between the solution outlet port 1012 and a dressing, and a fluid path 1030 between the negative-pressure port 1014 and a negative-pressure source. The fluid path 1030 may additionally couple the negative-pressure source to the dressing through the exudate container 1004 in some embodiments.

Each of the fluid path 1026, the fluid path 1028, and the fluid path 1030 may be comprised of more than one fluid conductor, coupled together through suitable interfaces. For example, in some embodiments, the fluid path 1026 may include an integrated fluid conductor molded into the exudate container 1004. In other embodiments, the fluid path 1026 may include a tube. A fluid conductor can be coupled on a first end to the solution inlet port 1010 and terminate on a second end with an interface 1032 through the exudate container 1004. Another fluid conductor may be coupled between the interface 1032 and the solution bag 1006. In other embodiments, the fluid path 1026 may be a tube, which can be coupled on a first end to the solution inlet port 1010, exit the exudate container 1004 through the interface 1032, and be coupled or configured to be coupled on a second end to the solution bag 1006. Similarly, in some embodiments, the fluid path 1028 may include an integral fluid conductor molded into the exudate container 1004. In other embodiments, the fluid path 1028 may include a tube. A fluid conductor can be coupled on a first end to the solution outlet port 1012 and terminate on a second end with an interface 1034 through the exudate container 1004. Another tube or fluid conductor may be coupled between the interface 1034 and a dressing to complete a fluid path to the dressing. In other embodiments, the fluid path 1028 may be a tube, which can be coupled on a first end to the solution outlet port 1012, exit the exudate container 1004 through the interface 1034, and be coupled or configured to be coupled on a second end to a dressing. The fluid path 1030 may similarly include an integrated fluid conductor or a tube coupled to a negative-pressure source through an interface 1036.

Figure 11:
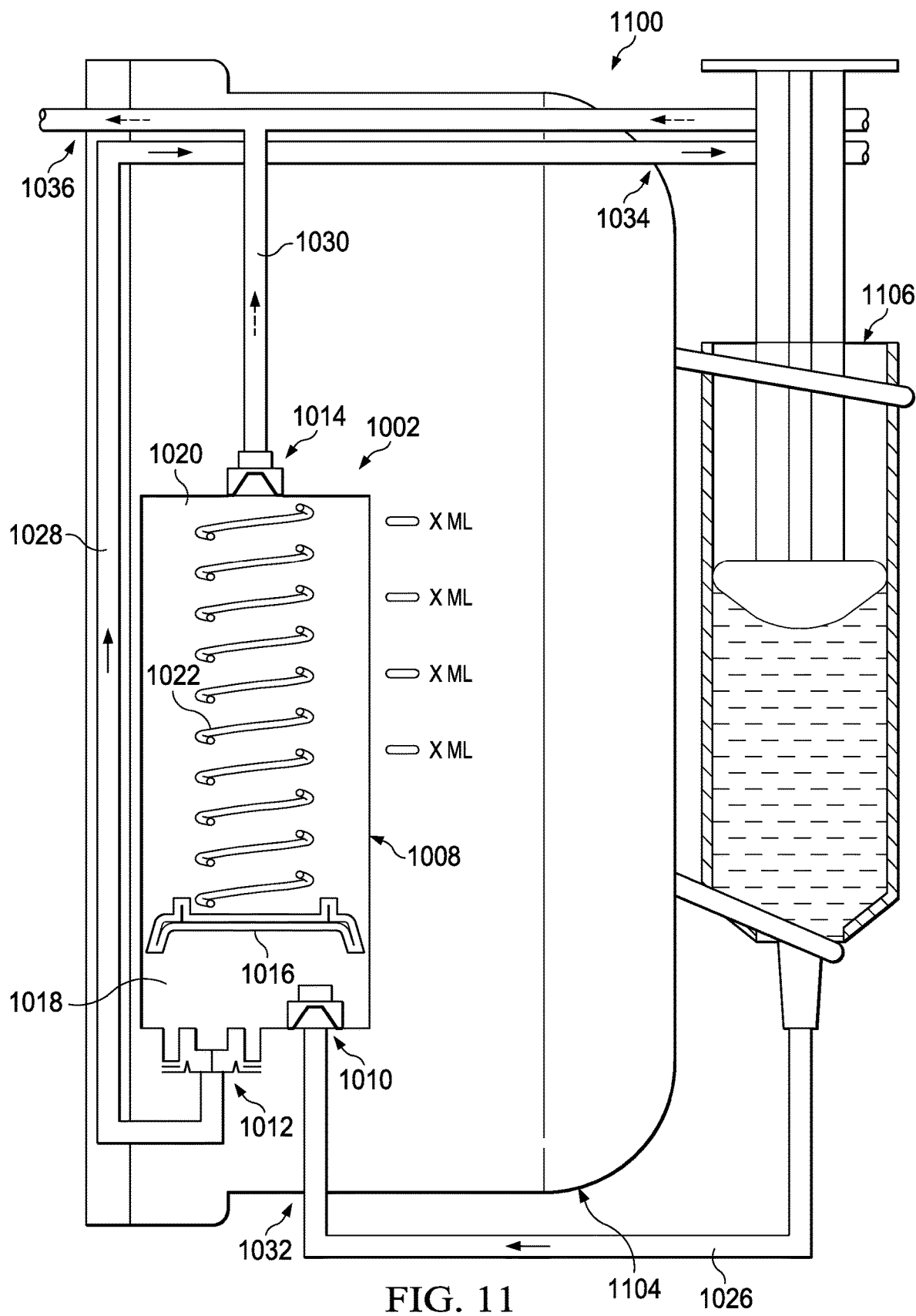
FIG. 11 is a schematic diagram illustrating another example embodiment of a fluid management system comprising the instillation regulator of FIG. 10 disposed within an exudate container.

FIG. 11 is a schematic diagram illustrating another example embodiment of a fluid management system 1100 comprising the installation regulator 1002 disposed within an exudate container 1104. The exudate container 1104 may be another example embodiment of the container 112 of FIG. 1. In some embodiments, the installation regulator 1002 may be fastened to a wall of the exudate container 1104, or may be integrally molded with the exudate container 1104. The fluid management system 1100 may also include an installation solution source, such as a syringe 1106. The syringe 1106 may be an example embodiment of the solution source 114 of FIG. 1. In some embodiments, the syringe 1106 may be externally mounted on the exudate container 1104, as illustrated in FIG. 10. In other embodiments, the syringe 1106 may be secured to a pole or other hanger, preferably in close proximity to the exudate container 1104. The syringe 1106 can prime the fluid management system 1100 with installation fluid that can be obtained from other sources, such as from larger containers or from multiple containers. The syringe 1106 may also be advantageous for accurately recording dosages of installation solution administered through the fluid management system 1100.

Figure 12:
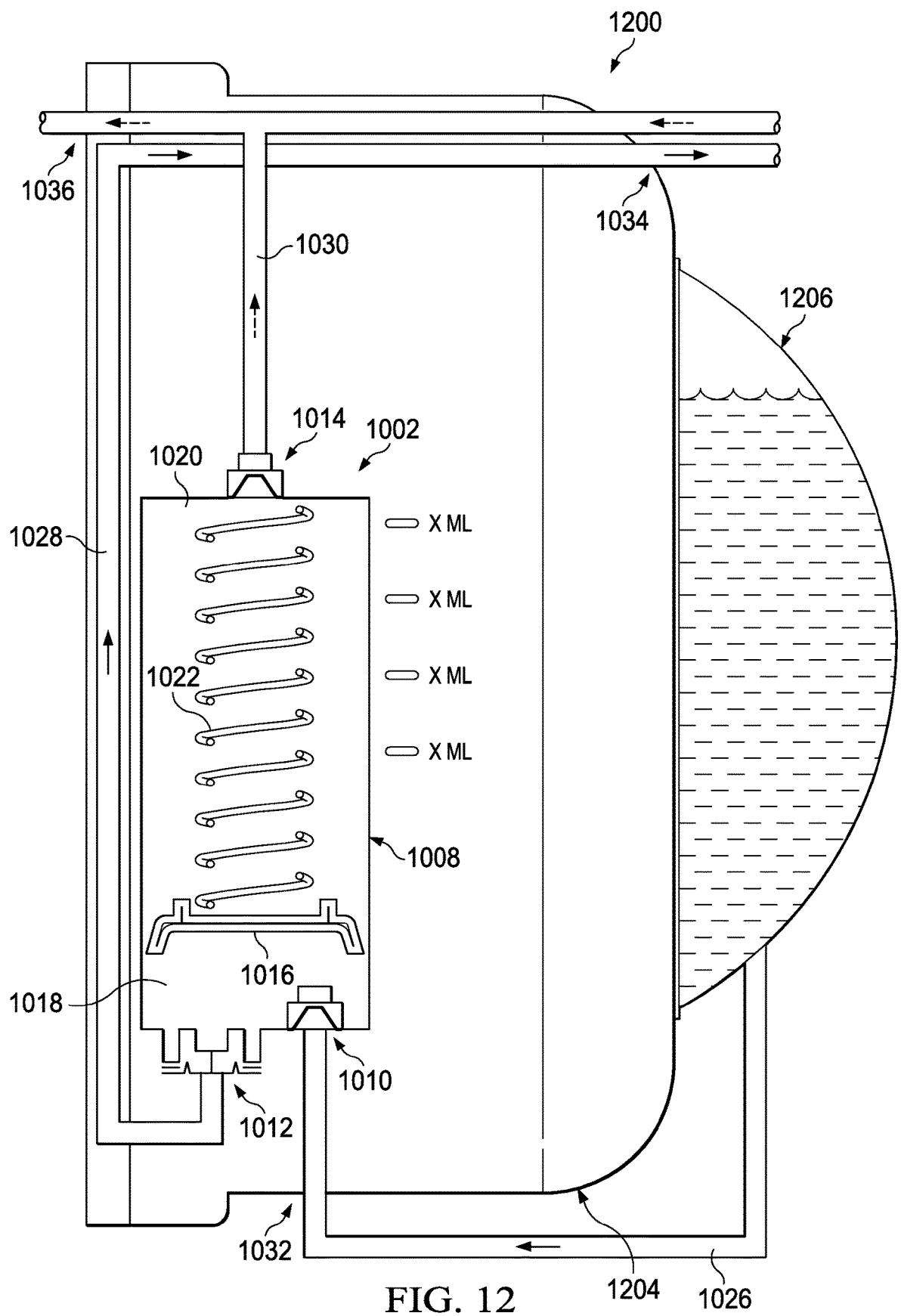
FIG. 12 is a schematic diagram illustrating another alternative embodiment of a fluid management system.

FIG. 12 is a schematic diagram illustrating another alternative embodiment of a fluid management system 1200. The fluid management system 1200 may include the installation regulator 1002 integrated with an exudate container 1204. The exudate container 1204 may be another example embodiment of the container 112 of FIG. 1. In some embodiments, the installation regulator 1002 may be fastened to a wall of the exudate container 1204, or may be integrally molded with the exudate container 1204. The fluid management system 1200 may also include an installation solution source, such as a solution container 1206. The solution container 1206 may be another example embodiment of the solution source 114 of FIG. 1. In some embodiments, the solution container 1206 may be integrated with the exudate container 1204 to provide a single disposable unit. For example, in some embodiments, the solution container 1206 may be a pouch comprising a suitable plastic or liquid-impermeable film welded or otherwise secured to an external surface of the exudate container 1204. In other embodiments, the solution container 1206 may be a rigid plastic integrally molded with the exudate container 1204. The fluid path 1026 may also be integrated in the exudate container 1204 in some embodiments to reduce external tubes.

Figure 13:
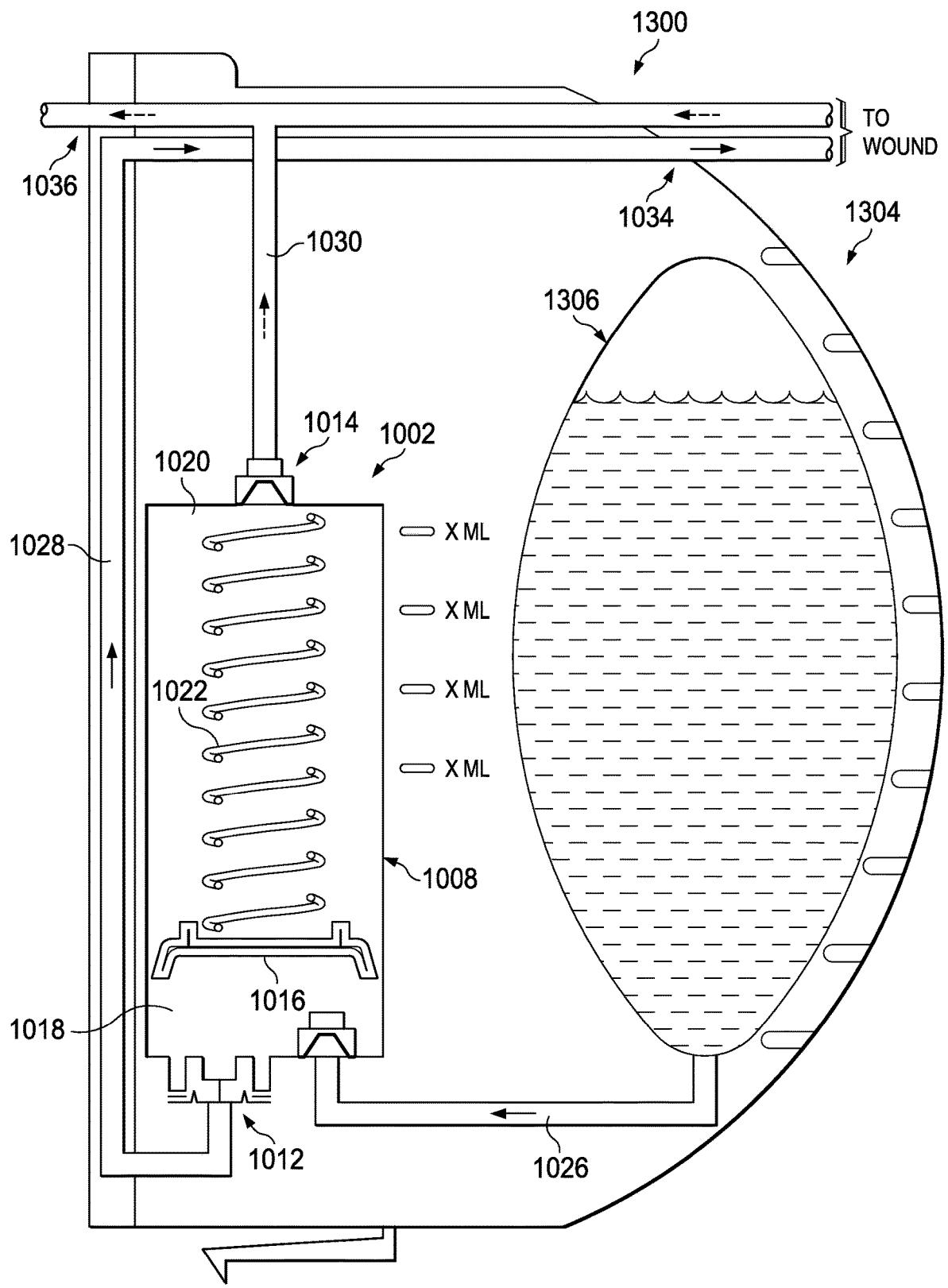
FIG. 13 is a schematic diagram illustrating another alternative embodiment of a fluid management system.

FIG. 13 is a schematic diagram illustrating another alternative embodiment of a fluid management system 1300. The fluid management system 1300 may include the installation regulator 1002 disposed within an exudate container 1304. The exudate container 1304 may be an example embodiment of the container 112 of FIG. 1. In some embodiments, the installation regulator 1002 may be fastened to a wall of the exudate container 1304, or may be integrally molded with the exudate container 1304. The fluid management system 1300 may also include an installation solution source, such as a solution container 1306. The solution container 1306 may be an example embodiment of the solution source 114 of FIG. 1. In some embodiments, the solution container 1306 may be integrated with the exudate container 1304 to provide a single disposable unit. For example, in some embodiments, the solution container 1306 may be a flexible pouch disposed within an interior space of the exudate container 1304. Disposing the solution container 1306 within the exudate container 1304 may be advantageous for transport and storage, and may also prevent tampering and use of uncontrolled instillation solution. The volume displaced by the solution container 1306 can be reduced as instillation solution is delivered to a tissue site, thereby increasing the free volume in the exudate container 1304 available for collecting exudate and used instillation solution. A non-return valve can prevent the solution container 1306 from expanding under negative pressure in the exudate container 1304.

Figure 14:
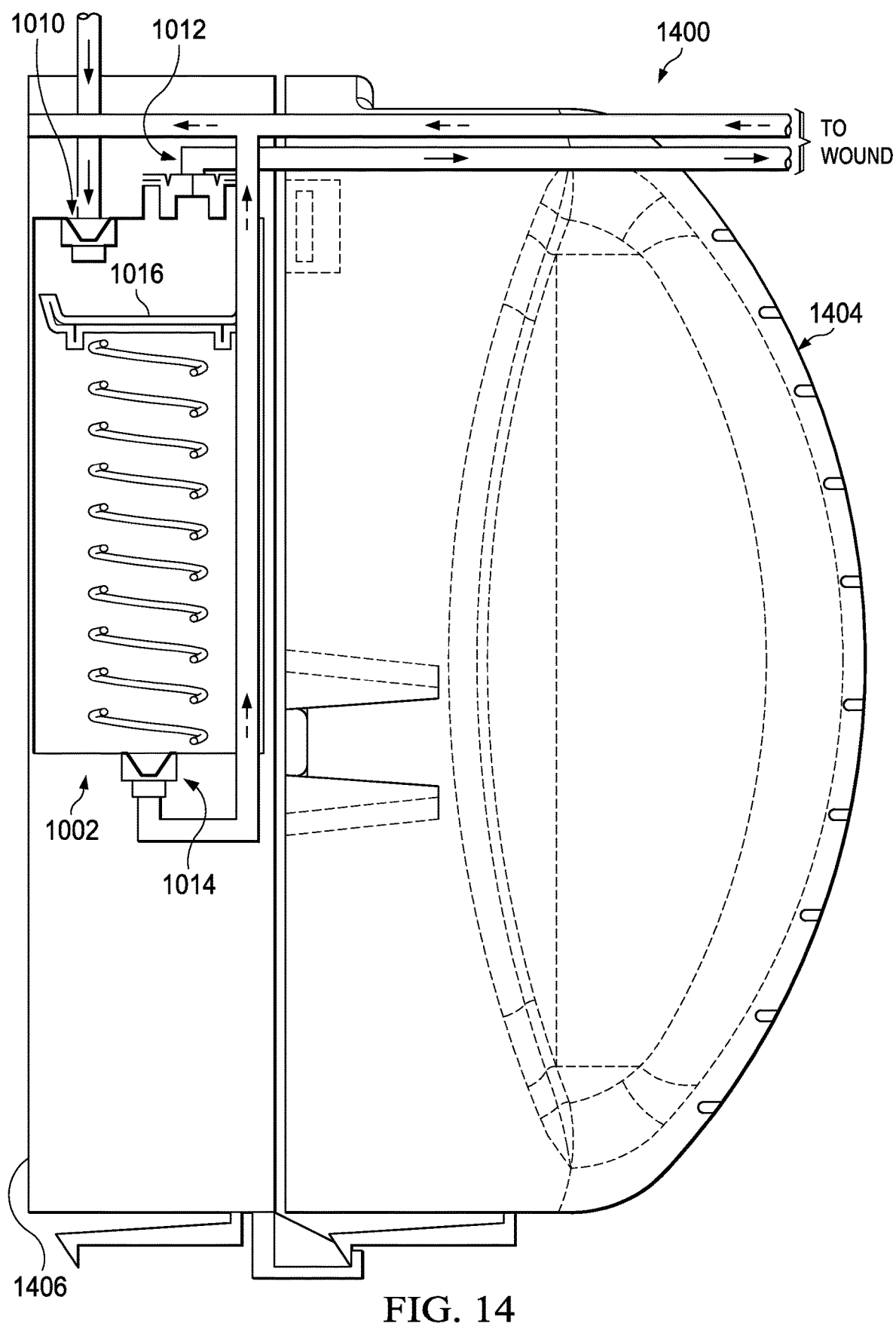
FIG. 14 is a schematic diagram illustrating yet another example embodiment of a fluid management system.

FIG. 14 is a schematic diagram illustrating yet another example embodiment of a fluid management system 1400. The fluid management system 1400 may include the instillation regulator 1002 coupled externally to an exudate container 1404. For example, in some embodiments the instillation regulator 1002 may be disposed within, integrated with, or coupled to an adapter housing 1406, which can be coupled to the exudate container 1404. The exudate container 1404 and the adapter housing 1406 may each be configured with suitable interfaces to fluidly couple the solution inlet port 1010 to an instillation solution source (not shown in FIG. 14), and to fluidly couple the solution outlet port 1012 to a dressing (not shown in FIG. 14). The exudate container 1404 and the adapter housing 1406 may also include suitable interfaces for fluidly coupling a negative-pressure source (not shown in FIG. 14) to the negative-pressure port 1014 and to a dressing. In some embodiments, the instillation regulator 1002 or the adapter housing 1406 may be detached from the exudate container 1404 and re-used, particularly for a single patient.

Figure 15:
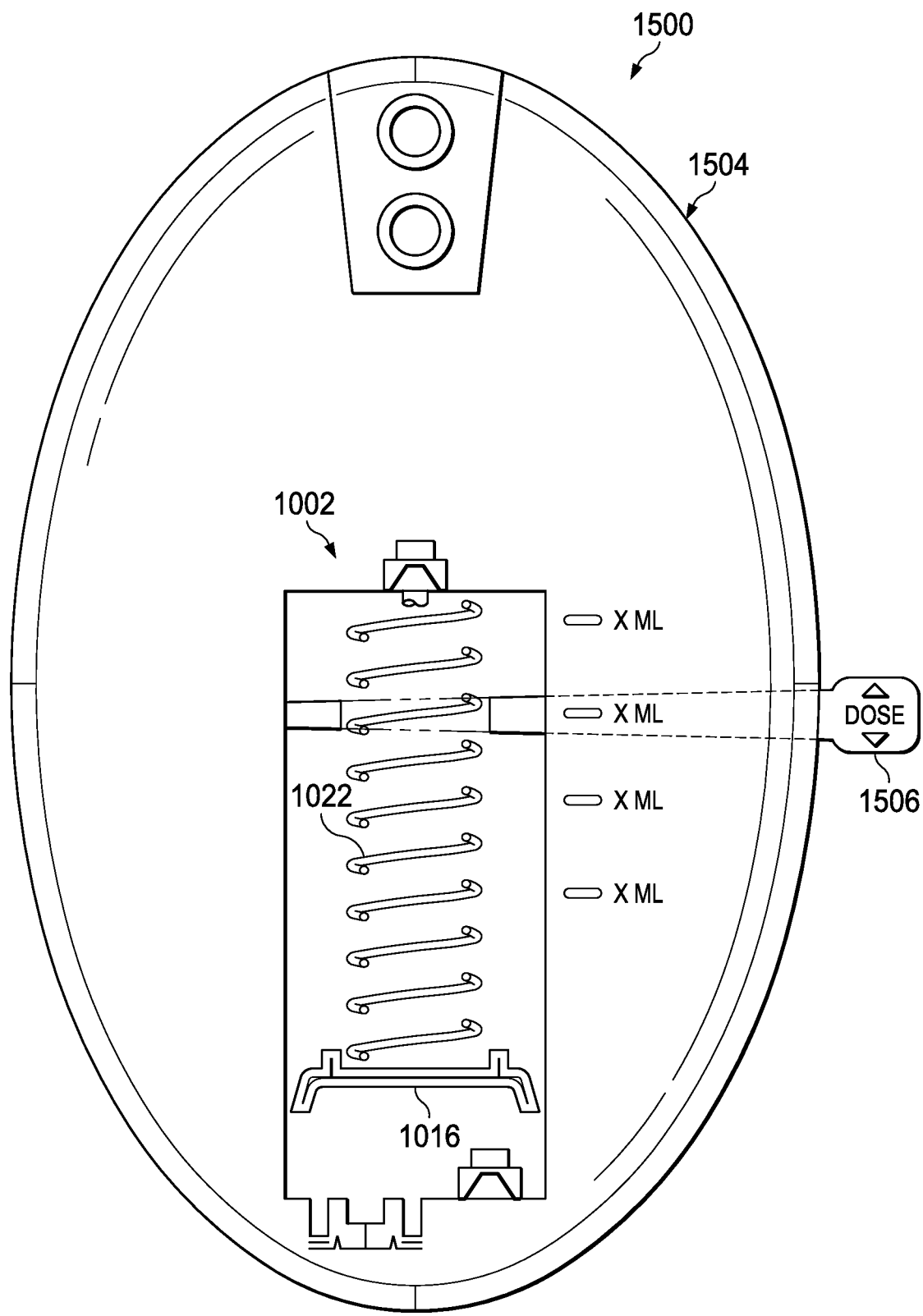
FIG. 15 is a schematic diagram illustrating additional details that may be associated with some embodiments of a fluid management system.

FIG. 15 is a schematic diagram illustrating additional details that may be associated with some embodiments of a fluid management system 1500. The fluid management system 1500 may be analogous to any of the previously described embodiments of a fluid management system, or any combination of features previously described. For example, the fluid management system 1500 may include the instillation regulator 1002 disposed within an exudate container 1504. The exudate container 1504 may be an example embodiment of the container 112 of FIG. 1. In some embodiments, the instillation regulator 1002 may be fastened to a wall of the exudate container 1504, or may be integrally molded with the exudate container 1504. The fluid management system 1500 may optionally include a means for controlling or adjusting a dosage of instillation solution. For example, a pin or adjustable lever 1506 may limit the range of motion of the piston 1016 in some embodiments. In other example embodiments, the spring rate of the spring 1022 may be increased or decreased.

Figure 16:
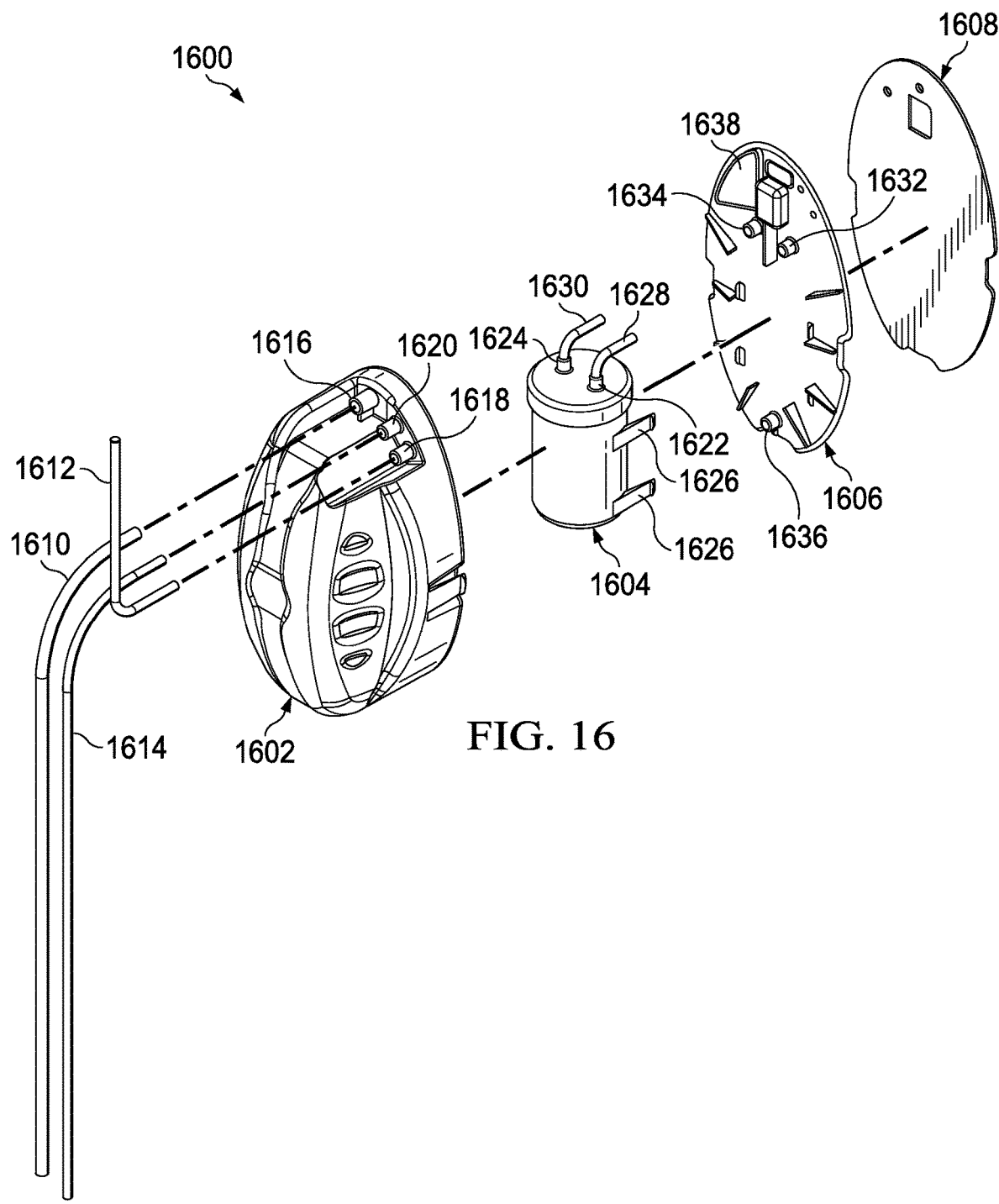
FIG. 16 is an assembly view illustrating an example embodiment of a fluid management system.

FIG. 16 is an assembly view illustrating an example embodiment of a fluid management system 1600. The fluid management system 1600 may include a container housing 1602, an instillation regulator 1604, a panel 1606, and a seal 1608. The container housing 1602 and the panel 1606 are preferably constructed from a material that is impermeable to fluid, such as a rigid or semi-rigid plastic. The seal 1608 preferably comprises a material that is relatively pliable and impermeable to fluid. For example, the seal 1608 may be manufactured from a non-porous polyester film, preferably having a thickness between 0.1 millimeters and 0.2 millimeters. The seal 1608 also preferably comprises an adhesive or other suitable means for attaching the seal 1608 to the panel 1606. For example, the seal 1608 may include an acrylic adhesive applied to one side, preferably having a thickness of about 0.15 millimeters. In some embodiments, the seal 1608 may be an adhesive label or integrated with product labeling.

The fluid management system 1600 may also include tubes or other fluid conductors for fluidly coupling the fluid management system 1600 to a tissue site or other components of a therapy system, such as the therapy system 100. For example, as illustrated in FIG. 16, the fluid management system 1600 may include a tube 1610 for coupling the container housing 1602 to a tissue site, a tube 1612 for coupling the container housing 1602 to an instillation solution source, and another tube 1614 for coupling the container housing 1602 to a tissue site.

In some embodiments, the container housing 1602 may include fluid ports adapted for coupling to tubes or other fluid conductors. For example, the container housing 1602 may include a fluid port 1616 adapted for coupling to the tube 1610, a fluid port 1618 adapted for coupling to the tube 1612, and a fluid port 1620 adapted for coupling to the tube 1614.

In some embodiments, the instillation regulator 1604 may be similar or analogous to the instillation regulator 1002 in many respects. For example, the instillation regulator 1604 may have fluid ports, such as a solution outlet port 1622 and a solution inlet port 1624, analogous to the solution outlet port 216 and the solution inlet port 214, respectively. The instillation regulator 1604 may also have retention clips 1626 adapted to mechanically couple the instillation regulator 1604 to the panel 1606. A tube or other fluid conductor may also be coupled to the solution outlet port 1622 and the solution inlet port 1624. For example, as illustrated in FIG. 16, a tube 1628 may be coupled to the solution outlet port 1622 and a tube 1630 may be coupled to the solution inlet port 1624.

In some embodiments, the panel 1606 may also include fluid ports adapted for coupling to a tube or other fluid conductor. For example, as shown in FIG. 16, the panel 1606 may include a port 1632, a port 1634, and a port 1636. A hydrophobic filter 1638 may also be coupled to or integral with some embodiments of the panel 1606.

Figure 17:
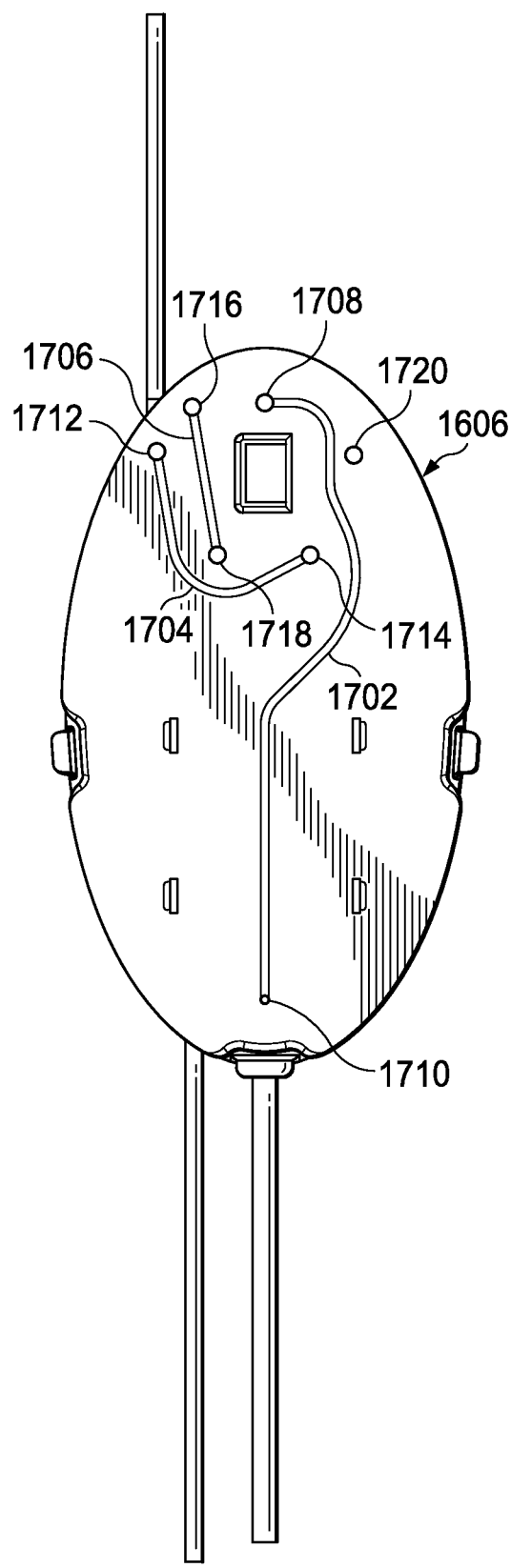
FIG. 17 is a rear view of a panel of FIG. 16, illustrating additional details that may be associated with some embodiments.

FIG. 17 is a rear view of the panel 1606 of FIG. 16, illustrating additional details that may be associated with some embodiments. As illustrated in FIG. 17, fluid channels may be integrated into some embodiments of the panel 1606. For example, the panel 1606 of FIG. 17 may include a channel 1702, a channel 1704, and a channel 1706. In some embodiments, each of the channel 1702, the channel 1704, and the channel 1706 may be an open channel, as shown in FIG. 17. Such an open channel may, for example, be formed as a groove, furrow, cut, depression, or gutter in the panel 1606. In some embodiments, an open channel may have a rectangular, semi-circular, or trapezoidal cross-section, for example. A passage through the panel 1606 may also be disposed at each terminus of the channels 1702-1706 in some embodiments. For example, a passage 1708 may be disposed at a first terminus of the channel 1702, and a passage 1710 may be disposed at a second terminus of the channel 1702. Similarly, a passage 1712 may be disposed at a first terminus of the channel 1704 and a passage 1714 may be disposed at a second terminus of the channel 1704, and a passage 1716 and a passage 1718 may be disposed at opposing ends of the channel 1706. In the example embodiment of FIG. 17, some or all of the passages 1708-1718 may be fluidly coupled to a fluid port on the opposing side of the panel 1606. For example, the passage 1710 may be fluidly coupled to the port 1636, the passage 1714 may be fluidly coupled to the port 1634, and the passage 1718 may be fluidly coupled to the port 1632. The panel 1606 may include additional passages, such as a passage 1720, which can fluidly couple a first side of the panel 1606 to a second side of the panel 1606. In some embodiments, the passage 1720 can be fluidly coupled to the hydrophobic filter 1638.

The seal 1608 may be attached to the panel 1606 and cover the channels 1702-1706 to form integrated fluid conductors. For example, the seal 1608 may cover the channel 1702 to form an integrated fluid conductor between the passage 1708 and the passage 1710. The seal 1608 preferably covers and seals each of the channels 1702-1706, and each of the channels 1702-1706 is preferably deep enough to ensure that deformation of the seal under negative pressure does not cause the seal to block the channels 1702-1706.

Figure 18:
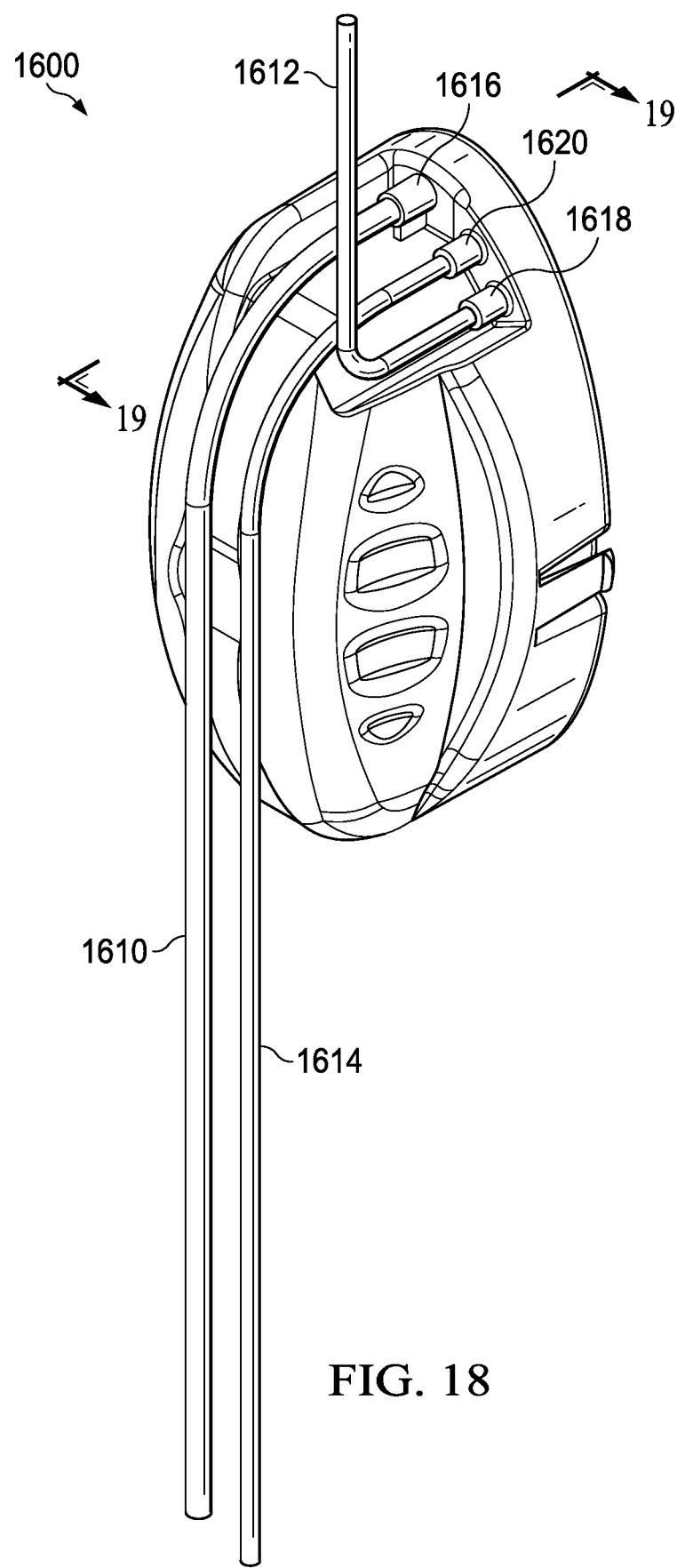
FIG. 18 is a perspective view of an example embodiment of the assembled fluid management system of FIG. 16.

FIG. 18 is a perspective view of an example embodiment of the assembled fluid management system 1600. As illustrated in FIG. 18, the tube 1610 may be coupled to the port 1616, the tube 1612 may be coupled to the port 1618, and the tube 1614 may be coupled to the port 1620.

Figure 19:
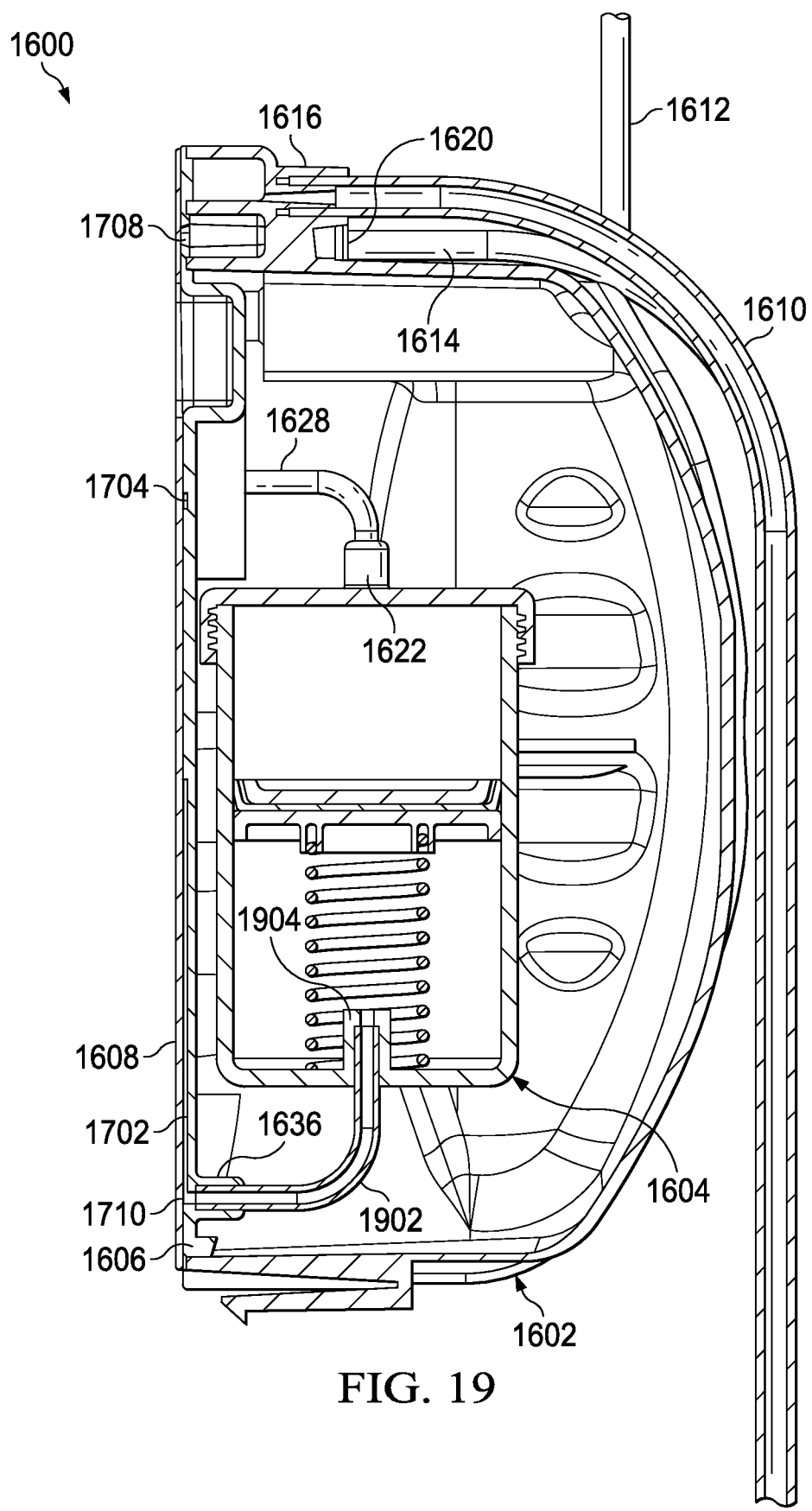
FIG. 19 is a section view of the fluid management system shown in FIG. 16 taken along line 19-19 of FIG. 18, illustrating additional details that may be associated with some embodiments.

FIG. 19 is a section view of the fluid management system 1600 taken along line 19-19 of FIG. 18, illustrating additional details that may be associated with some embodiments. As shown in the example embodiment of FIG. 19, the panel 1606 is preferably configured to be fastened to the container housing 1602 to enclose the installation regulator 1604 and form an exudate container, which may be suitable for use with some embodiments of the fluid management systems previously described. In some embodiments, for example, the fluid management system 1600 may be assembled to provide fluid paths analogous to the fluid path 1026, the fluid path 1028, and the fluid path 1030.

For example, a fluid path analogous to the fluid path 1026 may be provided by coupling a first end of the tube 1612 to the port 1618, and coupling a second end of the tube 1612 to an installation solution source, such as the solution bag 1006, the syringe 1106, or the solution container 1206. The port 1618 may provide a fluid path from the tube 1612 to the passage 1712, and the channel 1704 can provide a fluid path from the passage 1712 to the passage 1714. The passage 1714 can provide a fluid path from the channel 1704 to the port 1634. The tube 1630 can provide a fluid path between the port 1634 and the solution inlet port 1624, thereby completing a fluid path between the installation solution source and the solution inlet port 1624.

A fluid path analogous to the fluid path 1028 may also be assembled by coupling a first end of the tube 1614 to the port 1620, and coupling a second end of the tube 1614 to a dressing, such as the dressing 102. Assembled in this exemplary configuration, the tube 1628 can provide a fluid path between the solution outlet port 1622 and the port 1632. The port 1632 can provide a fluid path between the tube 1628 and the passage 1718, which can be in fluid communication with the channel 1706. The channel 1706 can provide a fluid path between the passage 1718 and the passage 1716, which can be in fluid communication with the port 1620, thereby completing a fluid path between the solution outlet port 1622 and the tube 1614.

In some embodiments, a fluid path analogous to the fluid path 1030 may be provided by fluidly coupling the passage 1720 to a negative-pressure source, such as the negative-pressure source 104, for example. Assembled in this exemplary configuration, the passage 1720 can provide a fluid path between a negative-pressure source and the interior of the container housing 1602, preferably through the hydrophobic filter 1638. The tube 1610 may be coupled to the port 1616, which can also be in fluid communication with the interior of the container housing 1602, thereby completing a fluid path between a negative-pressure source and the tube 1610. The tube 1610 can be fluidly coupled to a dressing or tissue site to extend the fluid path to the dressing or tissue site.

The tube 1610 preferably has at least two lumens, and the port 1616 may also have two lumens in some embodiments. For example, in some embodiments, a first lumen of the tube 1610 may be fluidly coupled to a first lumen of the port 1616 to deliver negative-pressure to a dressing or tissue site, and a second lumen of the tube 1610 may be fluidly coupled to a second lumen of the port 1616 to provide a feedback path for negative-pressure from a dressing or tissue site. The first lumen of the port 1616 may be in fluid communication with the interior of the container housing 1602, and the second lumen of the port 1616 may be fluidly coupled to passage 1708 when assembled. In this exemplary configuration, the passage 1708 may provide a fluid path between the second lumen of the port 1616 and the channel 1702. The channel 1702 can provide a fluid path between the passage 1708 and the passage 1710, which can be in fluid communication with the port 1636. A tube or other fluid conductor, such as a tube 1902, may provide a fluid path between the port 1636 and a negative-pressure port 1904 of the installation regulator 1604, thereby completing a fluid path between the second lumen of the tube 1610 and the negative-pressure port 1904.

Figure 20:
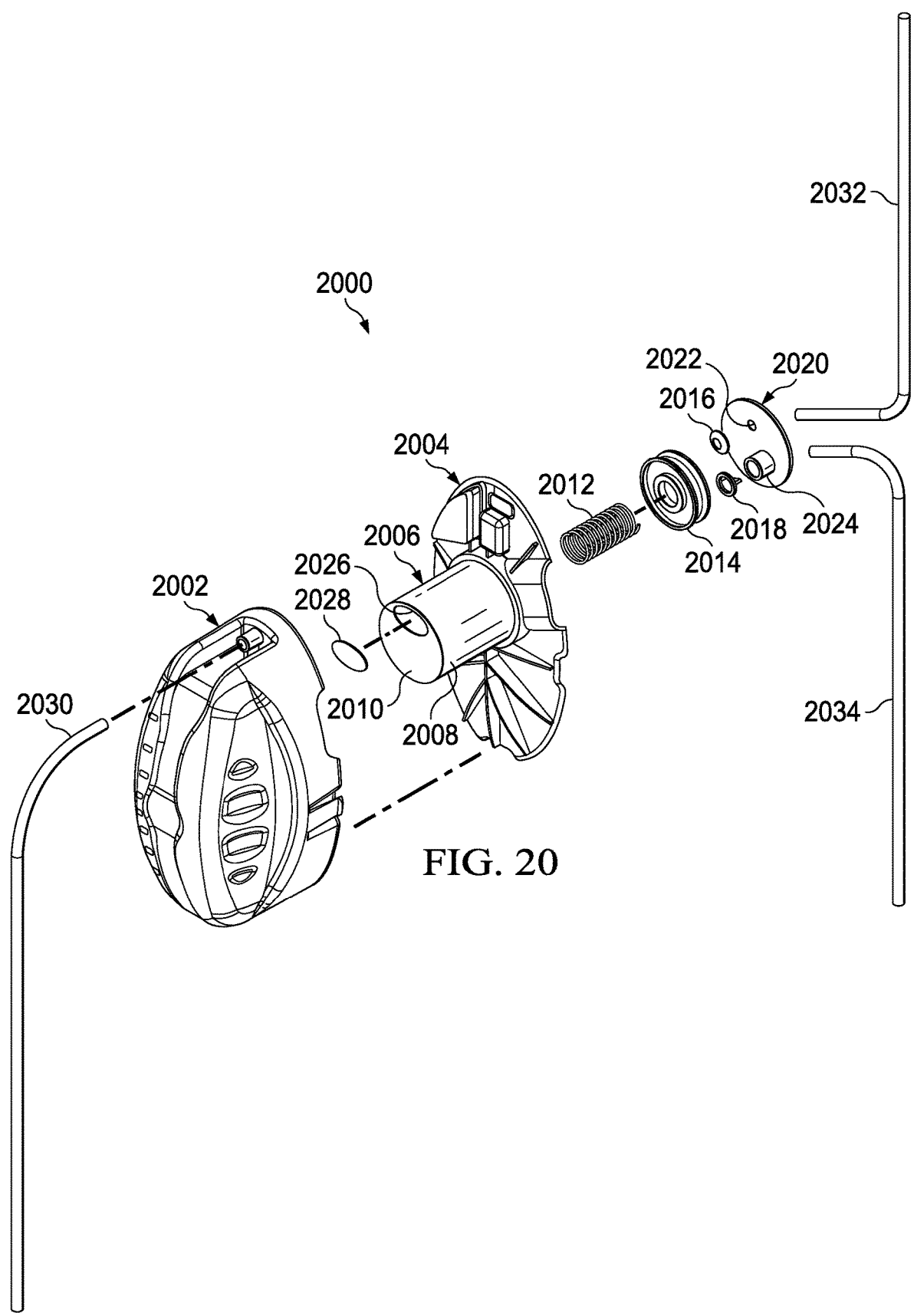
FIG. 20 is an assembly view illustrating another example embodiment of a fluid management system.

FIG. 20 is an assembly view illustrating another example embodiment of a fluid management system. The fluid management system 2000 of FIG. 20 may include a container housing 2002 and a panel 2004. The container housing 2002 and the panel 2004 are preferably constructed from a material that is impermeable to fluid, such as a rigid or semi-rigid plastic.

The fluid management system 2000 also preferably includes an installation regulator. For example, in some embodiments, a regulator body 2006 may be integrally molded with the panel 2004. In other embodiments, the regulator body 2006 may be inserted through an aperture in the panel 2004. In the example embodiment of FIG. 20, the regulator body 2006 has a cylindrical wall 2008 and a base 2010, and preferably has a major axis that is orthogonal to the plane of the panel 2004 to simplify molding.

Other regulator components, such as a spring 2012, a piston 2014, a first check valve 2016, a second check valve 2018, and a head 2020, may be assembled with the regulator body 2006 to provide an installation regulator that may be analogous to the installation regulator 1002 in many respects. For example, the piston 2014 may be disposed in the regulator body 2006 and partition the regulator body 2006 into two chambers, analogous to the first chamber 1018 and the second chamber 1020. The spring 2012 may be disposed between the piston 2014 and the base 2010, and the piston 2014 may reciprocate within the regulator body 2006. The head 2020 may be fastened to the regulator body 2006 to enclose the spring 2012 and the piston 2014. The head 2020 may also include a passage 2022 and a passage 2024. The base 2010 of the regulator body 2006 may include an aperture 2026, analogous to the negative-pressure port 1014. A hydrophobic filter 2028 is preferably disposed over the aperture 2026.

The fluid management system 2000 may also include tubes or other fluid conductors for fluidly coupling the fluid management system 2000 to a tissue site or other components of a therapy system, such as the therapy system 100. For example, as illustrated in FIG. 20, the fluid management system 2000 may include a tube 2030 for coupling the fluid management system 2000 to a tissue site, a tube 2032 for coupling the fluid management system 2000 to an instillation solution source, and another tube 2034 for coupling the fluid management system 2000 to a dressing or tissue site.

Figure 21:
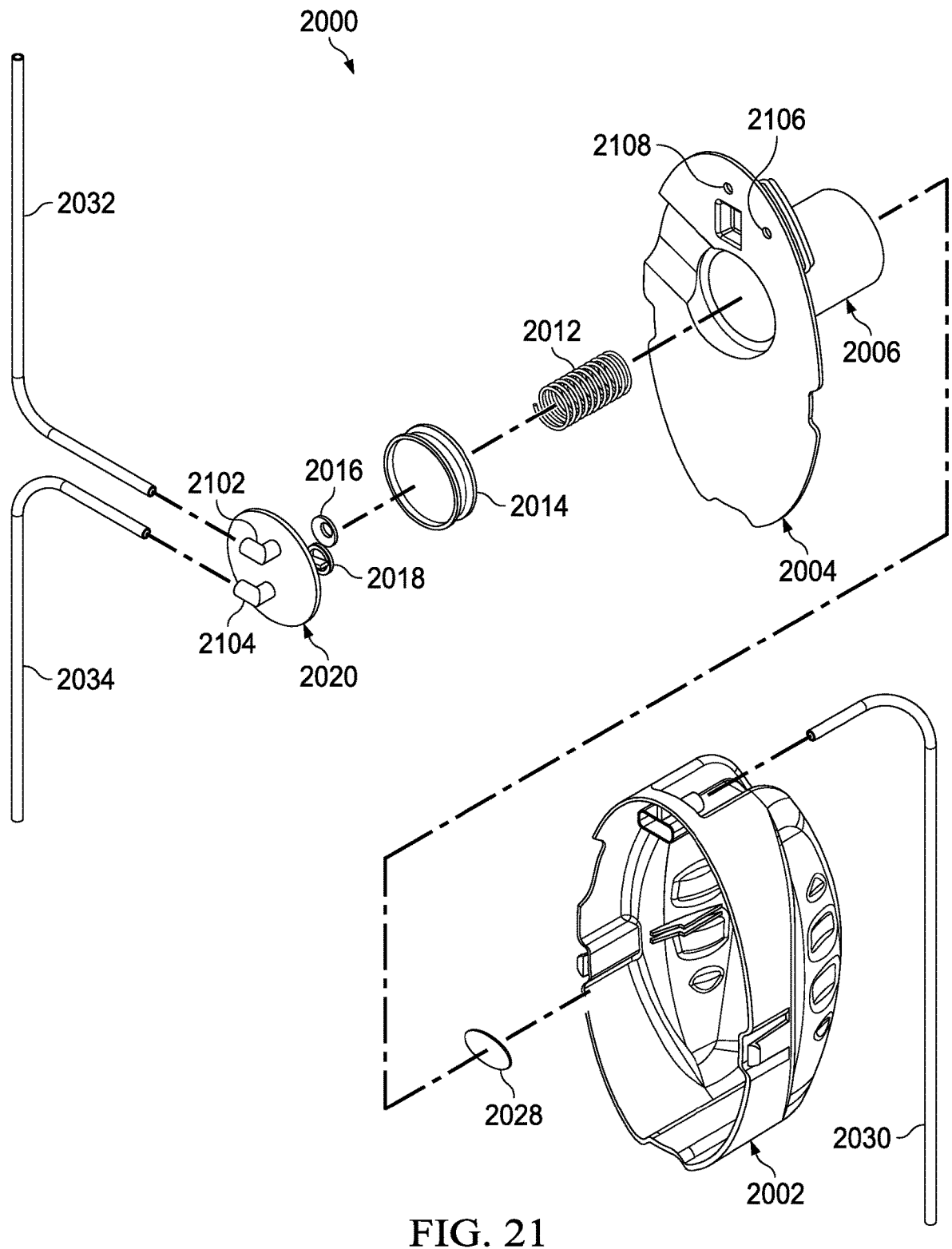
FIG. 21 is another assembly view illustrating additional details that may be associated with some embodiments of the fluid management system of FIG. 20.

FIG. 21 is another assembly view illustrating additional details that may be associated with some embodiments of the fluid management system 2000. As illustrated in the example embodiment of FIG. 21, the head 2020 may include a solution inlet port 2102 and a solution outlet port 2104, analogous to the solution inlet port 1010 and the solution outlet port 1012, respectively. The solution inlet port 2102 may be fluidly coupled to the passage 2022, and the solution outlet port 2104 may be fluidly coupled to the passage 2024. In some embodiments, the panel 2004 may also include additional passages, such as a passage 2106 and a passage 2108, as shown in the example embodiment of FIG. 21.

The panel 2004 is preferably configured to be fastened to the container housing 2002 to form an exudate container, which may be suitable for use with some embodiments of the fluid management systems previously described. In some embodiments, for example, the fluid management system 2000 may be assembled to provide fluid paths analogous to the fluid path 1026, the fluid path 1028, and the fluid path 1030.

For example, a fluid path analogous to the fluid path 1026 may be provided by coupling a first end of the tube 2032 to the solution inlet port 2102, and coupling a second end of the tube 2032 to an instillation solution source, such as the solution bag 1006, the syringe 1106, or the solution container 1206. The port 2102 may provide a fluid path from the tube 2032 to the passage 2022, which can be fluidly coupled to a chamber formed by the piston 2014 and the head 2020.

A fluid path analogous to the fluid path 1028 may also be assembled by coupling a first end of the tube 2034 to the solution outlet port 2104, and coupling a second end of the tube 2034 to a dressing, such as the dressing 102. The passage 2024 can provide a path between the solution outlet port 2104 and the chamber formed by the piston 2014 and the head 2020.

In some embodiments, a fluid path analogous to the fluid path 1030 may be provided by fluidly coupling the passage 2106 to a negative-pressure source, such as the negative-pressure source 104, for example. The passage 2106 may be in fluid communication with the interior of the container housing 2002, preferably through a hydrophobic filter. The aperture 2026 can also be in fluid communication with the interior of the container housing 2002. Thus, the interior of the container housing 2002 can provide a fluid path between the passage 2106 and the aperture 2026. The hydrophobic filter 2028 preferably provides a fluid path for negative-pressure between the aperture 2026 and the interior of the container housing 2002, but substantially blocks the fluid path for exudate and other liquids.

The example systems, apparatuses, and methods described herein may provide significant advantages. For example, instillation solution can be applied reliably while reducing the size, complexity, and number of parts needed for effective negative-pressure therapy with instillation. Moreover, instillation therapy can be provided even if there is a fluid head height to overcome. Some embodiments can also eliminate or reduce the need for ancillary components, such as ancillary bags for instillation solution, providing a single disposable apparatus. Some embodiments can also use a single interface pad and tubeset.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. An apparatus for managing fluid in a system for negative-pressure therapy, the apparatus comprising:
   an exudate container;
   a solution source configured to provide a liquid solution; and
   an instillation regulator configured to be fluidly coupled to the exudate container and to the solution source, the instillation regulator configured to be actuated by negative pressure from a negative-pressure source, wherein the instillation regulator comprises:
   a housing configured to be coupled to the exudate container;
   a piston disposed in the housing and partitioning the housing into a first chamber and a second chamber;
   a solution inlet port configured to be fluidly coupled to the solution source and to the first chamber;
   a solution outlet port configured to be fluidly coupled to a dressing and to the first chamber; and
   a negative-pressure port configured to be fluidly coupled to the negative-pressure source and the second chamber;
   wherein the piston is configured to be actuated by negative pressure applied to the negative-pressure port during a negative-pressure interval to draw the liquid solution into the first chamber through the solution inlet port and to instill the liquid solution from the first chamber through the solution outlet port during a venting interval.

2. The apparatus of claim 1, wherein the instillation regulator is disposed within an interior space of the exudate container.

3. The apparatus of claim 1, wherein the instillation regulator is integrally molded with the exudate container.

4. The apparatus of claim 1, wherein the solution source is externally mounted on the exudate container.

5. The apparatus of claim 1, wherein the solution source is a syringe externally mounted on the exudate container.

6. The apparatus of claim 1, wherein the solution source is integral with the exudate container.

7. The apparatus of claim 1, wherein the solution source is disposed within an interior space of the exudate container.

8. The apparatus of claim 1, wherein the solution source is a flexible pouch disposed within an interior space of the exudate container.

9. A system for treating a tissue site, comprising:
a dressing configured to be placed on the tissue site;
an exudate container;
a negative-pressure source configured to be in fluid communication with the dressing and with the exudate container, the negative-pressure source configured for a negative-pressure interval and a venting interval;
a solution source configured to provide a liquid solution; and
an instillation regulator configured to be in fluid communication with the solution source and with the negative-pressure source, the instillation regulator configured to draw the liquid solution from the solution source into the instillation regulator by an application of negative-pressure from the negative-pressure source during the negative-pressure interval and to instill the liquid solution from the instillation regulator to the dressing during the venting interval;
wherein the instillation regulator comprises:
 a housing configured to be coupled to the exudate container;
 a piston disposed in the housing and partitioning the housing into a first chamber and a second chamber;
 a solution inlet port configured to be coupled to the solution source and to the first chamber;
 a solution outlet port configured to be coupled to the dressing and to the first chamber; and
 a negative-pressure port configured to be coupled to the negative-pressure source and the second chamber;
wherein the piston is configured to be actuated by negative pressure applied to the negative-pressure port during a negative-pressure interval to draw the liquid solution into the first chamber through the solution inlet port and to instill the liquid solution from the first chamber through the solution outlet port during a venting interval.

10. The system of claim 9, wherein the solution source is externally mounted on the exudate container.

11. The system of claim 9, wherein the solution source is a syringe configured to be coupled to an external surface of the exudate container.

12. The system of claim 9, wherein the solution source is integral with the exudate container.

13. The system of claim 9, wherein the solution source is disposed within the exudate container.

14. The system of claim 9, wherein the solution source is a flexible pouch disposed within the exudate container.

15. The system of claim 9, wherein the instillation regulator is disposed between the negative-pressure source and the exudate container.

16. The system of claim 9, wherein the instillation regulator is disposed within an interior space of the exudate container.

17. A method for treating a tissue site, the method comprising:
applying a dressing to the tissue site;
coupling a negative-pressure source to the dressing, the negative-pressure source configured to provide a negative-pressure interval and a venting interval;
coupling an instillation regulator to the negative-pressure source and to the dressing, the instillation regulator comprising:
 a housing;
 a piston disposed in the housing and partitioning the housing into a first chamber and a second chamber;
 a solution inlet port fluidly coupled to the first chamber;
 a solution outlet port fluidly coupled to the dressing and to the first chamber; and
 a negative-pressure port fluidly coupled to the negative-pressure source and the second chamber;
coupling a solution source to the solution inlet port, the solution source providing a liquid solution;
drawing the liquid solution into the first chamber through the solution inlet port from the solution source during the negative-pressure interval; and
instilling the liquid solution from the first chamber through the solution outlet port to the dressing during the venting interval.

18. The system of claim 9, wherein the instillation regulator is integrally molded with the exudate container.

* * * * *